(12) United States Patent
Woodford

(10) Patent No.: US 9,173,575 B2
(45) Date of Patent: Nov. 3, 2015

(54) DETERMINING HEMODYNAMIC PERFORMANCE

(76) Inventor: Stephen Woodford, Wooywooy (AU)

( * ) Notice: Subject to any disclaimer, the term of this patent is extended or adjusted under 35 U.S.C. 154(b) by 0 days.

(21) Appl. No.: 13/378,353

(22) PCT Filed: Jun. 17, 2010

(86) PCT No.: PCT/AU2010/000748
§ 371 (c)(1), (2), (4) Date: Feb. 8, 2012

(87) PCT Pub. No.: WO2010/144961
PCT Pub. Date: Dec. 23, 2010

(65) Prior Publication Data
US 2012/0130697 A1    May 24, 2012
US 2013/0024176 A2    Jan. 24, 2013

Related U.S. Application Data

(60) Provisional application No. 61/218,053, filed on Jun. 17, 2009.

(51) Int. Cl.
G01N 33/48    (2006.01)
G01N 31/00    (2006.01)
(Continued)

(52) U.S. Cl.
CPC .............. *A61B 5/0205* (2013.01); *A61B 5/029* (2013.01); *A61B 5/02028* (2013.01); *A61B 5/412* (2013.01); *G06F 17/10* (2013.01); *G06F 19/12* (2013.01); *G06F 19/26* (2013.01); *G06F 19/32* (2013.01); *G06F 19/345* (2013.01); *G06F 19/3437* (2013.01); *G06F 19/3443* (2013.01);
(Continued)

(58) Field of Classification Search
None
See application file for complete search history.

(56) References Cited

U.S. PATENT DOCUMENTS 5,103,828 A   4/1992   Sramek
5,551,435 A   9/1996   Sramek
(Continued)

FOREIGN PATENT DOCUMENTS

GB    2279253 A      1/1995
JP    S61-272042 A   12/1986
(Continued)

OTHER PUBLICATIONS

Lang et al. Systemic vascular resistance: an unreliable index of left ventricular afterload. Circulation, vol. 74, 1986, pp. 1114-1123.*
(Continued)

*Primary Examiner* — Russell S Negin
(74) *Attorney, Agent, or Firm* — Knobbe Martens Olson & Bear LLP

(57) ABSTRACT

A method for determining haemodynamic performance in a human or animal subject comprises receiving at a processor data representing haemodynamic variables measured from the subject over time. The haemodynamic variables comprise at least two of Systemic Perfusion Pressure (SPP), Systemic Vascular Resistance (SVR), Cardiac Output (CO), Heart Rate (HR) and Stroke Volume (SV). The data are processed to produce a display signal for causing a display device to present a visual mapping relating the haemodynamic variables according to the relationship SPP=CO×SVR and the visual mapping is displayed on a display device. The visual mapping may be corrected Heart Rate (HR) or include a second mapping which facilitates an adjustment to take account of HR.

42 Claims, 32 Drawing Sheets

(51) Int. Cl.

| | |
|---|---|
| *G01N 33/50* | (2006.01) |
| *A61B 5/0205* | (2006.01) |
| *G06F 19/00* | (2011.01) |
| *G06F 19/26* | (2011.01) |
| *G06F 19/12* | (2011.01) |
| *G06F 17/10* | (2006.01) |
| *A61B 5/00* | (2006.01) |
| *A61B 5/02* | (2006.01) |
| *A61B 5/029* | (2006.01) |
| *A61B 5/021* | (2006.01) |
| *A61B 5/024* | (2006.01) |

(52) U.S. Cl.
CPC ............... *A61B 5/021* (2013.01); *A61B 5/024* (2013.01); *A61B 5/743* (2013.01); *G06F 19/3431* (2013.01)

(56) References Cited

U.S. PATENT DOCUMENTS

| | | | |
|---|---|---|---|
| 5,743,268 | A | 4/1998 | Kabal |
| 6,743,172 | B1 | 6/2004 | Blike |
| 7,226,602 | B2 * | 6/2007 | Whitehead et al. ........ 424/218.1 |
| 2005/0090753 | A1 | 4/2005 | Goor et al. |
| 2008/0287753 | A1 | 11/2008 | Parlikar et al. |
| 2009/0124867 | A1 | 5/2009 | Hirsh et al. |
| 2009/0131805 | A1 | 5/2009 | O'Brien et al. |
| 2009/0221923 | A1 | 9/2009 | Uemura et al. |

FOREIGN PATENT DOCUMENTS

| | | |
|---|---|---|
| JP | 10-270242 | 9/1998 |
| JP | 2005-501590 A | 1/2005 |
| JP | 2005-507701 A | 3/2005 |
| JP | 2009-514583 A | 4/2009 |
| WO | WO 01/67948 A2 * | 9/2001 |
| WO | WO 03/020131 A1 | 3/2003 |
| WO | WO 2006/054343 A1 | 5/2006 |
| WO | WO 2007/054841 A1 | 5/2007 |
| WO | WO2007/060559 A2 | 5/2007 |
| WO | WO 2009/063446 A2 | 5/2009 |
| WO | WO2009/107007 A1 | 9/2009 |

OTHER PUBLICATIONS

Becker et al, Fuzzy logic approaches to intelligent alarms, Magazine, Nov. 1994, pp. 710-716, vol. 13, No. 5, IEEE Engineering in Medicine and Biology Magazine.

Paul N. Kizakevich et al., Beat-by-beat Monitoring of Systemic Vascular Resistance during Head-Up Tilt for Assessment of Orthostatic Stress Response, 1994, pp. 82-87, Seventh Annual IEEE Symposium on Computer-Based Medical Systems.

M J Harrison, Effect of age on physiological variables during anaesthesia, online, 2006, Australian and New Zealand College of Anaesthetists Annual Scientific Meeting, http://www.anzca.edue.au/events/asm/asm2006/harrison_3.htm>.

International Search Report issued by the European Patent Office dated May 28, 2009, 3 pages.

International Search Report issued by the Australian Patent Office dated Aug. 4, 2010, 3 pages.

Ramirez et al., "Prognostic Value of Hemodynamic Findings from Impedance Cardiography in Hypertensive Stroke" American Journal of Hypertension, Ltd. Feb. 2005, vol. 18, No. 2, part 2, pp. 65S-72S.

European Search Report dated May 20, 2014, issued in connection with related European Patent Application 11848199.3.

Watanabe et al., "Coronary artery disease". Jun. 5, 2014 in 7 pages.

Japanese Notification of Reasons for Refusal dated Jun. 5, 2014 issued in connection with corresponding Japanese Patent Application No. 2012-515287.

European Search Report dated Oct. 2, 2014, issued in connection with corresponding European Patent Application No. 10788506.3.

* cited by examiner

|  | Type 1 (Circulatory failure with cardiac compensation) | Type 2 (Circulatory failure with failure of compensation) | Type 3 (Pure Cardiac Failure) |
|---|---|---|---|
| SVR | Decreased | Decreased | No Change |
| CO | Increased | No Change | Decreased |
| SPP (MAP-CVP) | No Change | Decreased | Decreased |

FIG. 31

| Age | 60 | 70 | 80 | 90 |
|---|---|---|---|---|
| Multiplier | 100 | 80 | 60 | 40 |
| Expected CO | 6000 | 5600 | 4800 | 3600 |

FIG. 32

| Age | 60 | 70 | 80 | 90 |
|---|---|---|---|---|
| Multiplier | 20 | 25 | 30 | 35 |
| SVR(SI) | 1200 | 1750 | 2400 | 3150 |

FIG. 33

DETERMINING HEMODYNAMIC PERFORMANCE

RELATED APPLICATIONS

This application is a U.S. National Phase of International Application No. PCT/AU2010/000748, filed Jun. 17, 2010, designating the U.S. and published in English on Dec. 23, 2010 as WO 2010/1449961, which claims the benefit of U.S. Provisional Patent Application 61/218,053 filed Jun. 17, 2009.

FIELD OF THE INVENTION

The present invention relates to a method, system and software product for determining haemodynamic performance in a human or animal subject. It relates particularly but not exclusively to a computer-implemented method, system and software product for generating a visual mapping of haemodynamic variables obtained from the subject, preferably in real time, for use in monitoring and improvement of therapeutic treatment.

BACKGROUND TO THE INVENTION

In a normal state of health, the human or animal body system continuously maintains physiological balance. Even during times of external influence due to disease, drugs, surgical intervention, trauma, cardiopulmonary bypass and the like, the body system auto regulates in order to maintain physiological balance. To achieve this balance, receptors throughout the body work to monitor and adjust haemodynamic variables such as pressure and flow.

In a non-optimal state of haemodynamic performance and where autoregulation has become impaired, the subject will often enter a state of shock manifesting in low blood pressure. In the clinical setting, the subject is monitored and therapy administered to ensure that there is sufficient flow in the body to reach all vital organs including the brain, heart and kidneys, so as to maintain adequate oxygen delivery to meet the metabolic needs of those organs. Failure to administer appropriate therapy leads to worsening of the patient's condition, ultimately leading to heart failure.

Traditionally, monitoring involves obtaining blood pressure measurements, together with measurements of oxygen saturation, heart rate ECG, and in the most severe cases, measuring cardiac output. Each of these parameters together with the clinician's assessment of physical signs give an indication of the subject's circulatory function e.g. during critical care, anaesthesia and surgery. Changes in circulatory function indicate that therapy must be adjusted in order to restore the function to more optimal values. Given the complexity and interaction of the organs of circulatory system, it is difficult for physicians to determine appropriate treatment when the subject's haemodynamic performance is being monitored using a variety of distinct variables viewed subjectively and individually. The principal obstacle to improving outcomes arises from the lack of a consensus about the appropriate haemodynamic goals in patient management. There is broad agreement that all patients require the same haemodynamic goals, but there is disagreement about which goals (in blood pressure, cardiac output, oxygenation) are critically important.

Physiology text books replicate two curves to describe the physiology of shock as illustrated in FIG. 1. During normal circulation, constant flow is maintained across a range of blood pressures. This is known as the "autoregulatory range".

Although the physiological mechanism for autoregulation is not fully understood, it is believed to be an intrinsic property of muscle (the "myogenic" hypothesis), and/or the result of physiological molecules (the "metabolic" hypothesis) which accumulate as pressure increases, and/or an effect of fluid crossing the barrier of the vessels and exerting increased pressure from outside to maintain flow at the lower level (the "tissue pressure" hypothesis).

Curve I represents the autoregulation curve in the "normal patient" having a mean arterial pressure of between 60 and 130 mmHg (normo-tensive patient). Curve II represents the autoregulation curve in the hypertensive patient. Here, constant flow is maintained at higher pressures hence the blood pressure range across which "autoregulation" occurs is shifted to the right. In the hypertensive patient, instead of auto regulating flow between a pressure range of 60 to 130 mmHg, in the hypertensive patient this range may be 80 to 150 mmHg.

Below the lower end of the autoregulatory range (region A), blood pressure and cardiac output fall. This is accepted to characterise low output hypotension. However, these curves do not describe the subject having high output hypotension (as occurs in sepsis). Instead, physicians have relied on graphical representations originating from the Guyton model. The Guyton model devised in the 1970s relied on the study of small numbers of laboratory animals and now inferior measurement techniques to explain how blood pressure and cardiac output were controlled, in order to devise treatments.

According to Guyton, in the circulation there is a constant matching of venous return (preload) and ventricular function (cardiac output). This is represented in FIG. 2. In the closed system of Guyton, venous return to the heart (Central Venous Pressure (CVP)/Right Arterial Pressure (RAP)) must match volume ejected by the heart. Any central venous pressure value can represent multiple "equilibrium points" between venous return and ventricular function. If venous return is increased the venous return curve shifts right, the central venous pressure is increased and the patient moves "up" the ventricular function curve (VFC). If the patient bleeds, venous return decreases, the curve shifts left and the new equilibrium point occurs at a lower point on the ventricular function curve.

In the clinical setting, physicians rely on individual vital sign monitoring systems as may be applied to the Guyton paradigm in order to determine appropriate therapies for subjects exhibiting characteristics of non-optimal haemodynamic function. Although the Guyton model intuitively matches clinical observations in a steady state situation, it does not adequately explain shock states and fails to account for physiological differences in e.g. the fit versus obese individual and the young versus elderly adult. Further, its use has prompted unproven theories that have been applied in the clinical setting, perhaps to the detriment of patients being treated. These deficiencies have been known for some time. One group of researchers is investigating use of an alternative resuscitation algorithm devised by Rivers (NEJM, 2001) which is the latest manifestation of 'goal directed therapy' the goal being to increase oxygen delivery on the as yet unproven assumption that this is the physiological purpose to which vasodilation and increased cardiac output is directed.

It would be desirable to provide an improved approach to monitoring subjects experiencing or likely to experience non-optimal haemodynamic performance. It would also be desirable to improve the manner in which therapies for restoring optimal haemodynamic performance are determined.

SUMMARY OF THE INVENTION

Viewed from one aspect, the present invention provides a computer-implemented method for determining haemodynamic performance in a human or animal subject comprising: receiving at a processor, first received data measured from the subject over time, from which at least two haemodynamic variables selected from the group including Systemic Perfusion Pressure (SPP), Systemic Vascular Resistance (SVR), and Cardiac Output (CO) may be derived either directly or indirectly; processing the first received data to produce a display signal, the display signal configured to cause a display device to present a visual mapping relating the at least two haemodynamic variables according to the relationship SPP=CO×SVR; and displaying the visual mapping on a display device. A computer program product embodied on a memory device may contain instructions causing a computer processor to perform the method.

The visual mapping may involve generating a graph plotting: CO in a first dimension (e.g. on a vertical axis) and SVR in a second dimension (e.g. on a horizontal axis); or SVR in a first dimension (e.g. on a vertical axis) and SPP in a second dimension (e.g. on a horizontal axis); or CO in a first dimension (e.g. on a vertical axis) and SPP in a second dimension (e.g. on a horizontal axis) although other formats are contemplated. Preferably the visual mapping includes one or more markers representing a scale for determining a value of a third haemodynamic variable.

In a preferred embodiment, the processor also receives data representing further haemodynamic variables including Heart Rate (HR) and Stroke Volume (SV), measured from the subject, either directly or indirectly, over a corresponding time period and the first received data is processed to adjust for HR. This is achieved by determining actual Systemic Vascular Resistance (aSVR) since SVR is not itself a real physiological entity. Rather, aSVR=SVR×HR, and, since CO=HR×SV, aSVR is related to SPP according to the relationship SPP=SV×aSVR. Thus, in a preferred embodiment the visual mapping plots SV in a first dimension (e.g. on a vertical axis) and aSVR in a second dimension (e.g. on a horizontal axis). CO may be indicated in a third dimension.

In one embodiment, the processor processes the data to produce a second display signal causing the display device to present simultaneously a second visual mapping. The visual mapping produced by the second display signal plots data according to the relationship CO=HR×SV. This mapping can provide insight into the elderly circulation.

In one embodiment, the processor is programmed to approximate and present on the display, an autoregulation zone on the mapping, preferably based on population specific data for persons having similar physiological profiles (e.g. of a given age and gender). The autoregulation zone may be displayed on the display device as a reference point for use by clinicians monitoring the subject in real time e.g. during surgery where therapies are directed to restoring the real-time mapping toward the age and gender specific autoregulation zone. Thus, the autoregulation zone may be used by the processor to determine an autoregulatory "zone" unique to the subject and toward which therapy may be directed. Preferably, data is obtained from the subject and processed in real-time although data collection and subsequent mapping may prove useful in many circumstances and particularly, in research.

It is to be understood, however, that an autoregulation zone to which a subject's therapy may be directed during resuscitation need not be unique to that subject. For example, in ambulatory or emergency scenarios there may be no data available which represents that subject's haemodynamic performance when in a state of health at rest and so that subject's unique autoregulation zone may not be known. Thus, the autoregulation zone referred to during resuscitation may be obtained from mapped data collected from a range of representative subjects having similar demographic characterisation. Indeed this approach may achieve significant improvements in clinical outcomes. Demographic characterisation may include matching one or more of e.g. age, gender, body mass index, body surface area and the like.

In one embodiment, the processor is programmed to identify in the data one or more patterns that may be associated with a physiological syndrome such as shock. The processor is programmed to classify the syndrome into one of type 1, type 2, type 3 or a combination thereof based on the one or more identified patterns in the subject's haemodynamic data.

The processor may also be programmed to quantify a deficit in one or more haemodynamic variables measured from the subject. The processor may be programmed to do this by, for example: determining a difference between the subject's mapped data and a pre-determined autoregulation zone unique to the subject; or determining a difference between the subject's data and a pre-determined autoregulation zone averaged from of a population of individuals; or extrapolating data values to a point of intersection representing a autoregulation zone unique to the subject.

Preferably, the processor is programmed to identify automatically non-optimal haemodynamic function in the subject. The processor may also be programmed to recommend therapeutic action to restore optimal haemodynamic function in the subject.

Viewed from another aspect, the present invention provides a system for evaluating haemodynamic function in a human or animal subject, the system including: one or more transducers for monitoring continuously over time, either directly or indirectly, haemodynamic variables of the subject selected from the group comprising Systemic Perfusion Pressure (SPP), Systemic Vascular Resistance (SVR) and Cardiac Output (CO) and generating one or more corresponding first data signals; a processor receiving the one or more first data signals and generating a display signal for a visual representation of the first data in which the at least two haemodynamic variables are mapped, preferably in an x-y mapping, according to the relationship SPP=CO×SVR; and a display device receiving the display signal and generating the visual representation; wherein haemodynamic function is determinable upon inspection of the visual representation. Preferably the visual representation includes one or more markers representing a scale for determining a value of a third haemodynamic variable.

In an embodiment the processor further receives data signals representing Heart Rate (HR) and Stroke Volume (SV) measured from the subject, either directly or indirectly, over a corresponding time period and adjusts the first data for HR by determining actual Systemic Vascular Resistance (aSVR) where aSVR=SVR×HR. Since CO=HR×SV, the SPP relationship can be re-expressed as SPP=SV×aSVR. The processor may produce a second display signal causing the display to present a second visual mapping of variables according to the relationship CO=HR×SV. The visual mappings may be displayed simultaneously.

In one embodiment, the system includes a mode selector for selecting a mode of visual representation of the data; wherein the mode is selected from: CO in a first dimension (e.g. on a vertical axis) and SVR in a second dimension (e.g. on a horizontal axis) (isobar nomogram); SVR in a first dimension (e.g. on a vertical axis) and SPP in a second dimension (e.g. on a horizontal axis) (isoflow nomogram); and CO in a first dimension (e.g. on a vertical axis) and SPP (isoresistance nomogram) in a second dimension (e.g. on a horizontal axis). The modes selectable by the mode selector may also include simultaneous display of the second visual mapping.

The system may include an analysis module for approximating an autoregulation zone unique to the subject based on the received data or a portion thereof. A diagnosis module may be provided to identify one or more patterns in the data associated with a physiological syndrome. In one embodiment, the physiological syndrome is shock and the diagnosis module uses the one or more identified patterns to classify the shock syndrome into one of: type 1, type 2, type 3 or a combination thereof.

An analysis module may be provided, for quantifying a deficit in one or more of the monitored haemodynamic variables from the subject. The techniques used by the system correspond to those in the preceding summary of the computer-implemented method. The system may further include an alert module configured to activate an alert automatically when non-optimal haemodynamic performance is detected.

Viewed from another aspect, the present invention provides a method for determining haemodynamic performance in a human or animal subject or in a group or human or animal subjects, comprising: generating a visual representation of data representing haemodynamic variables obtained from the subject or the group of subjects over time, said data representing two variables selected from the group including (i) Systemic Perfusion Pressure (SPP); (ii) Systemic Vascular Resistance (SVR); and (iii) Cardiac Output (CO); and approximating from the visual representation the subject's haemodynamic performance. Approximating the subject's haemodynamic performance may involve identifying patterns or trends (changes in the patterns) in the subject's data and/or, for example, estimating from the visual representation a corresponding value of the third variable.

Preferably, the visual representation provides a continuous mapping of haemodynamic performance in real time. To assist, the visual representation may include one or more markers for quantification of the third variable, wherein the one or more markers are determined according to the relationship: SPP=CO×SVR.

In one embodiment, n the haemodynamic data represented in the visual representation is corrected for Heart Rate (HR) by determining actual Systemic Vascular Resistance (aSVR) where aSVR=SVR×HR and CO=HR×SV and the SPP relationship is re-expressed as SPP=SV×aSVR. Thus, the visual representation may contain data representing Stroke Volume (SV) in a first dimension and aSVR in a second dimension.

Preferably the haemodynamic data is obtained and used to generate the visual representation in real time. The method may also involve approximating an autoregulation zone unique to the subject.

Patterns identified in the data may be associated with a physiological syndrome such as shock. In one embodiment, one or more identified patterns are used to classify the shock into one of type 1, type 2, type 3 or a combination thereof.

The method may also involve the step of quantifying a deficit in one or more of the haemodynamic variables in the subject, using techniques proposed in relation to the previously summarised computer-implemented method.

In one embodiment, the method further includes automatically identifying non-optimal haemodynamic performance in the subject and/or titrating or tailoring therapeutic treatment for the subject so as to restore haemodynamic performance toward the subject's autoregulation zone. Preferably, an alert is automatically activated when the subject's haemodynamic performance is non-optimal.

The method may be used to evaluate the effect of pharmacological therapy on haemodynamic function, and rate of action. The method may also be used to devise automatically, a treatment plan or suggested therapy for restoring non-optimal haemodynamic performance toward an optimal state.

The discussion of the background to the invention included herein including reference to documents, acts, materials, devices, articles and the like is intended to explain the context of the present invention. This is not to be taken as an admission or a suggestion that any of the material referred to was published, known or part of the common general knowledge in as at the priority date of any of the claims.

BRIEF DESCRIPTION OF THE DRAWINGS

Embodiments of the invention will now be described by reference to the accompanying drawings. It is to be understood that the drawings are provided for the purpose of describing features of the invention only. They do not supersede the generality of the preceding parts of the description and do not limit the scope of the invention as it may be defined in claims appended hereto or in any future application claiming priority here from.

FIG. 6a shows a pattern for Type 1 shock; FIG. 6b shows a pattern for Type 2 shock; FIG. 6c shows a pattern for Type 3 shock and FIG. 6d shoes the aggregation of FIGS. 6a-6c.

FIG. 7a shows a pattern for Type 1 shock; FIG. 7b shows a pattern for Type 2 shock; FIG. 7c shows a pattern for Type 3 shock and FIG. 7d is an aggregation of FIGS. 7a-7c.

FIG. 8a shows a pattern for Type 1 shock; FIG. 8b shows a pattern for Type 2 shock; FIG. 8c shows a pattern for Type 3 shock and FIG. 8d shoes the aggregation of FIGS. 8a-8c.

FIG. 31 represents indicators of 3 types of shock as may be classified according to an embodiment of the invention.

FIG. 32 sets out the inventor's "60-70-80-90/100-80-60-40 rule for estimating expected CO in elderly females.

FIG. 33 sets out the inventor's 60-70-80-90/20-25-30-35 rule of thumb for estimating average SVR in elderly females.

DETAILED DESCRIPTION

The autoregulation curve according to Guyton has hitherto been accepted as a generic representation of the dynamics of flow across a single organ. However, the model and its users have been ambivalent to its relevance and applicability to the systemic circulation which comprises numerous organs and organ microvascular beds. The total circulatory system is a system with much greater complexity than a single organ and may be considered, in the context of an equivalent circuit model, as multiple resistors in "parallel". In view of this complexity, there has been reluctance in practice to assume that the generic autoregulation curve, as it applies to the single organ, has relevance to the systemic circulation as a whole.

Figure 2:
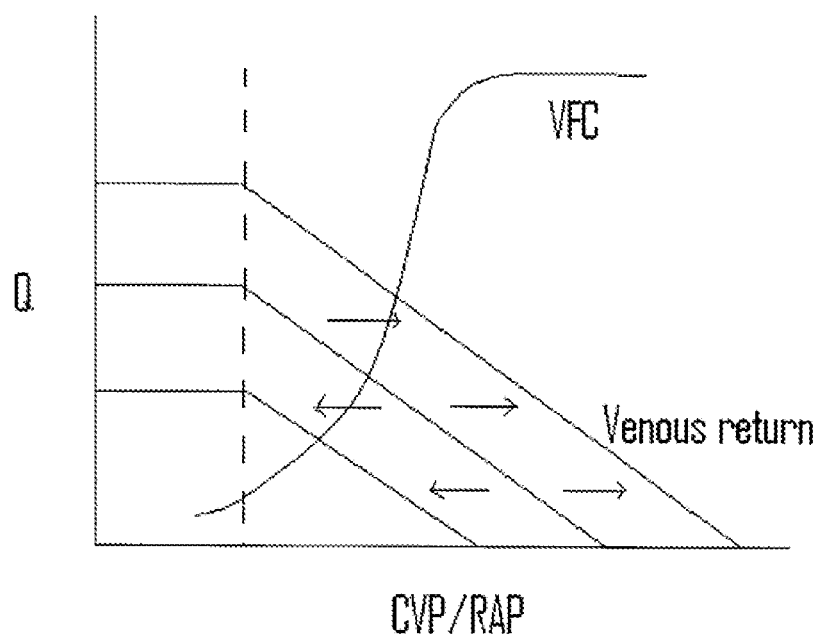
FIG. 2 represents the autoregulation curve according to Guyton.

Based on the current understanding of the circulation, Central Venous Pressure (CVP) is treated as a surrogate for intravascular filling, i.e. the higher the CVP, the 'fuller' the circulation. Guyton's model assumes that the dynamic relationship that describes the heart and circulation is reflected in the changing relationship between venous return and cardiac function curves. Guyton's graph (FIG. 2) representing 'high output hypotension' taken alone would suggest that as volume is added, the patient's haemodynamic performance moves to the right and moves 'up' the corresponding Ventricular Function Curve (VFC). However, it is not possible to extrapolate from the VFC curve to the arterial pressure. If the CVP rises, then the perfusion pressure gradient falls, so tissue blood flow falls. If the patient is 'volume depleted' and volume is added, the situation is improved only if the increase in arterial pressure is greater than any increase in venous pressure, i.e. if the MAP–CVP gradient is increased, so perfusion pressure is improved.

Systemic Perfusion Pressure (SPP) is the driving pressure gradient in the systemic circulation. It is the difference (typically measured in mmHg) between the central venous pressure (CVP) and the mean arterial pressure (MAP) when referenced to atmospheric pressure and is calculated as SPP=MAP–CVP. Currently, normal adult values for MAP and CVP are considered to be 65 mmHg and 10-12 mmHg respectively although little thought has been given to the pressure gradient that these values give rise to (i.e. 53 to 55 mmHg).

Systemic Vascular Resistance (SVR) is the resistance to blood flow presented by the vasculature. It is calculated indirectly by dividing measurements of the pressure gradient across the vasculature (SPP) by the rate of flow (Q, or Cardiac Output, CO) through the vessel. Thus SVR may be expressed in mmHg/L/min or dyne·sec/cm$^5$ (SI units). Normal adult values are 900 to 1600 dyne·sec/cm$^5$.

Systemic Vascular Resistance Index (SVR Index) is SVR compensated to body size. Normal adult values are 1760 to 2600 dyne sec/cm$^5$/m$^2$.

Stroke Volume (SV) is the volume of blood ejected by the left ventricle for each contraction of the heart.

Heart Rate (HR) is the number of left ventricular contractions occurring per minute.

Cardiac Output (CO) is measured in L/min and is the volume of blood that the left ventricle pumps into the circulation per minute. CO is calculated as the product of HR and SV. Normal adult values are 4.0 to 8.0 L/min.

The pressure gradient, SPP, which drives flow in the systemic circulation, is critical to maintaining haemodynamic performance. It has been observed that when a patient goes onto cardio-pulmonary bypass the pressure gradient falls to 30 mmHg but not below. Similarly, it has been observed that SPP falls to 30 mmHg just before circulatory arrest. Accordingly, as long as the SPP value (i.e. net pressure gradient driving the circulation) exceeds 30 mmHg, cardiac output can be relatively normal.

However when the SPP gradient drops to 30 mmHg death ensues. This minimum pressure gradient which is compatible with life is referred to as the "closing pressure" of the circulation. It represents the intrinsic resistance to flow attributable to the microvasculature, particularly the capillary beds. The implications of this are significant.

Because the importance of the 'closing pressure' has been overlooked in Guyton's model and the importance of the SPP has not been recognized, the focus in the past has been entirely on blood oxygen content and therapy has been directed to correcting the mismatch between oxygen supply and tissue oxygen demand. Thus, using existing theories a patient with high output hypotension and tissue acidaemia is believed to be exhibiting inadequate blood oxygen carriage. In contrast, by observing haemodynamic performance according to the present invention it can be postulated that the fundamental problem is an inadequate tissue perfusion pressure gradient (i.e. insufficient SPP). It is further postulated that tissue dysfunction and failure occurs as the pressure gradient drops.

To further complicate and highlight the inadequacies of the traditional understanding and models of circulation, the circulation has hitherto been understood in terms of 2 pumps: the left ventricle and right ventricle. These pumps drive blood through the tubes of the vasculature to deliver oxygen to the organs. Based on this existing model, the CVP must represent the same information in health or disease. The present invention gives rise to a different paradigm, in which it is hypothesized that the two pumps at work are the cardiac pump and the vascular pump.

Both the cardiac pump and the vascular pump are substantially under neural control. When the heart ejects blood into the aorta during systole, it enables coronary blood flow during diastole but it also stores 'potential energy' in the form of blood pressure in the vascular pump which is in turn used to deliver continuous flow of blood throughout the cardiac cycle.

The vascular pump is a dynamic organ, regulated by its neural inervation and sensitive to circulating toxins and pharmacologic agents. Embodiments of the present invention may be used to distinguish shock states arising primarily from cardiac pump failure from shock states which are primarily the result of vascular pump failure. Where the fundamental pattern can be identified, a much clearer diagnosis and strategy for correction can be devised.

Ohm's law relates voltage, current and resistance in electrical circuits and can be expressed as:

$$V=IR \qquad \text{(Equation 1)}$$

where V is voltage; I is current and R is resistance. Substituting equivalent variables from the systemic circulation where voltage corresponds to Systemic Perfusion Pressure (SPP); current corresponds to Cardiac Output (CO) (i.e. flow); and resistance corresponds to Systemic Vascular Resistance (SVR) gives:

$$SPP=CO \times SVR. \qquad \text{(Equation 2)}$$

Based on Ohm's Law, the present invention provides a method of generating a visual mapping of haemodynamic variables measured from a subject which gives an immediate indication of the subject's haemodynamic performance. Thus, a method of determining haemodynamic performance in a human or animal subject comprises receiving data representing haemodynamic variables measured from the subject over time, said haemodynamic variables comprising at least two of Systemic Perfusion Pressure (SPP), Systemic Vascular Resistance (SVR), Cardiac Output (CO), Heart Rate (HR) and Stroke Volume (SV) and processing the data to produce a display of a visual mapping relating the haemodynamic variables according to the relationship SPP=CO×SVR. Preferably the method is computer implemented.

The inventor has discovered that Ohm's Law is not simply a general equation describing the behaviour of the circulation, but that by continuous collection of pressure, flow and resistance data, a unique profile can be constructed that is specific to an individual patient and has devised a method and system for generating that profile. Indeed, the fact that every individual's circulation behaves differently is a significant discovery resulting from application of the invention. Medical literature assumes that there is a generally correct profile of action of vasoactive drugs, whereas the application of the present invention reveals that the activity profile of various pharmacological agents varies between individuals and that the variation is significant for different patient populations.

The inventor has also found that many of the defining characteristics of vasoactive drugs are not real, but result from a failure to correct for the effect of HR on the calculation of SVR.

Figure 1:
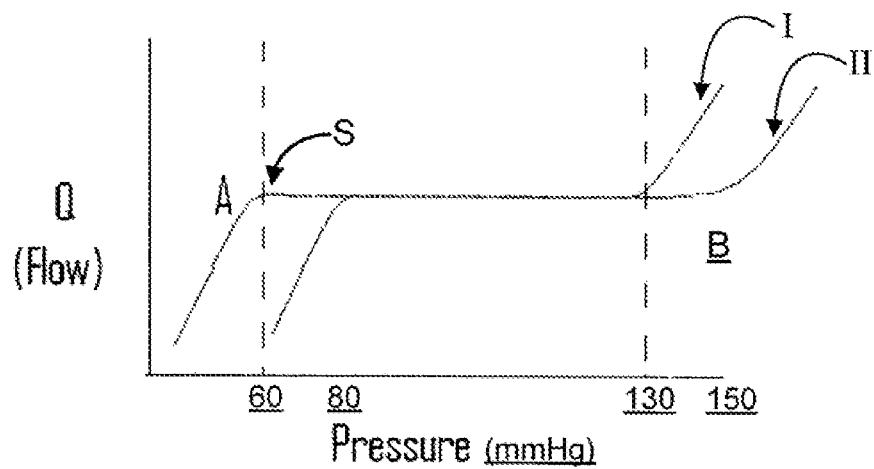
FIG. 1 represents the generic autoregulation curves which indicate the autoregulation function of (I) the normo-tensive and (II) the hypertensive subject respectively.

Referring again to the autoregulation curve I in FIG. 1, for a healthy patient at rest the lower inflection point S corresponds to the autoregulatory 'set point' for haemodynamic function where the cardiac output (CO) (i.e. flow) remains constant over a normal range of pressure. This corresponds to the horizontal section of the curve. Below the lower inflection point S, CO falls with pressure. This area is designated by the letter A and represents the drop off zone below which organ dysfunction occurs. Above the horizontal section of the curve CO increases with pressure. This region is designated by the letter B.

By applying Equation 1 to the systemic circulation it can be deduced that CO (i.e. flow) remains constant in the horizontal region of the curve because SVR is increasing linearly. Therefore, substituting k (a constant) for CO, Ohm's Law as applied to the circulation becomes:

$$SPP=k(SVR) \qquad \text{Equation 3)}$$

Figure 3A:
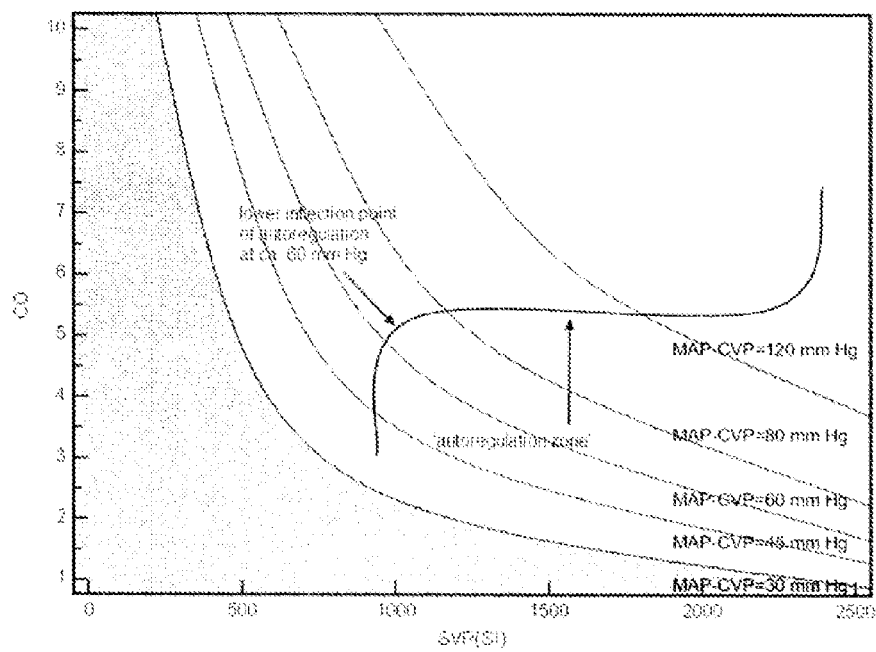
FIGS. 3a to 3c show examples of visual representations of haemodynamic performance using haemodynamic mapping in three different formats according to embodiments of the invention.

By plotting SVR on the x-axis against CO on the y-axis of a visual mapping (e.g. FIG. 3a), the autoregulation range must appear in the region of the curve represented by a substantially horizontal line. Since the equation SPP=CO×SVR has the general form a=xy, where x=CO and y=SVR, if a is given a particular value (e.g. 30 mmHg, 45 mmHg, 60 mmHg, 80 mmHg), the variables can be related as illustrated in FIG. 3a. This isobar nomogram provides a time-sensitive mapping of the interplay between pressure, flow and vascular resistance and discloses a great deal of information about haemodynamic patterns in the individual.

In a preferred embodiment as shown, a series of markers or "isobars" represent a scale for corresponding values of SPP (i.e. 30 mmHg, 45 mmHg, 60 mmHg, 80 mmHg, 120 mmHg), which increase with distance from the origin. By superimposing a stream of haemodynamic data on this "format" of mapping and colour coding the data points to reflect e.g. an intervention and/or a time window, a significant amount of information can be gleaned by visual inspection of the mapping.

Figure 3B:
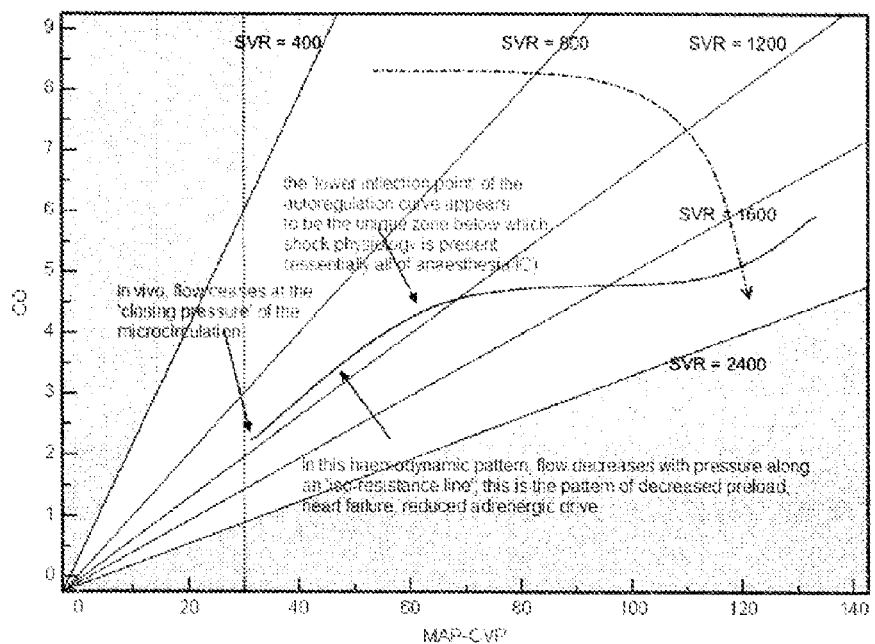

Another format of mapping shown in FIG. 3b which represents the relationship between blood flow and pressure across a physiological range by plotting values for CO on the vertical axis and values for SPP on the horizontal axis. This may be referred to as an iso-resistance nomogram. A series of iso-resistance markers are provided in the mapping (i.e. SVR becomes the 'z-variable' within the graph). The broken vertical line indicates the 'closing pressure' below which there is no systemic flow.

Figure 3C:
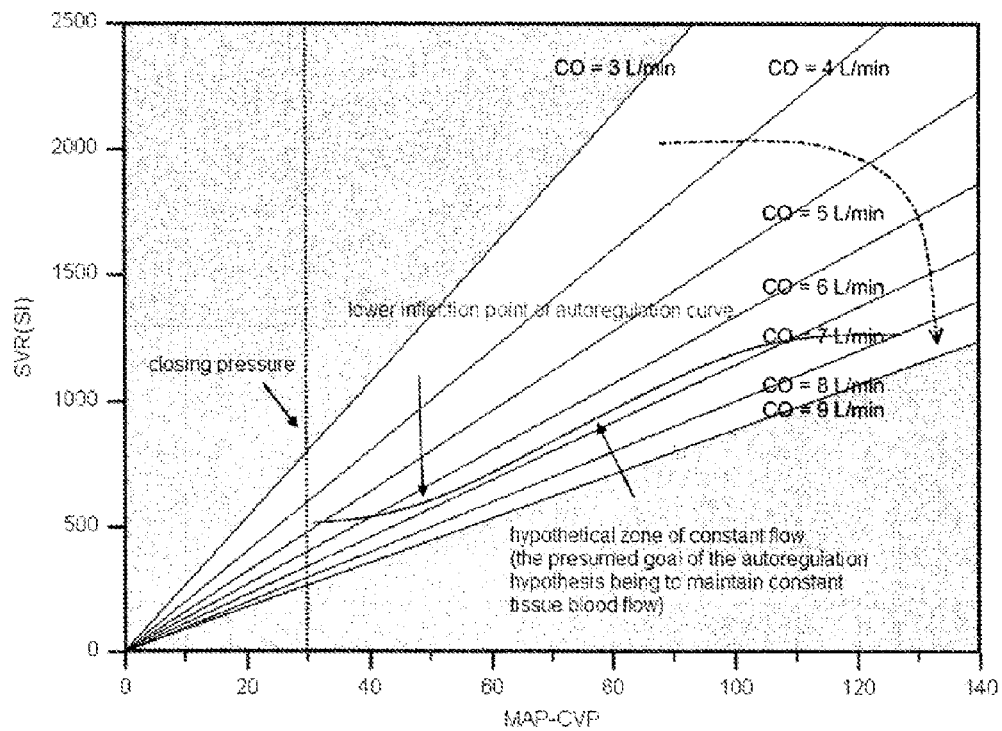

Another form of mapping is shown in FIG. 3c where SVR is plotted on the vertical axis against SPP on the horizontal axis. Superimposed on this mapping is a "classical" autoregulation curve based on the Guyton model. Below the 'lower inflection point' pressure is flow-dependent. The plateau region represents one discrete pattern but does not provide any insight at all into cerebral and renal blood flow preservation in whole populations. The broken vertical line again represents the 'closing pressure' of the microcirculatory system below which there is no flow. In each case, the broken arrow represents the direction of increase of the third variable (i.e. SVR in FIG. 3b; CO in FIG. 3c).

Figure 4:
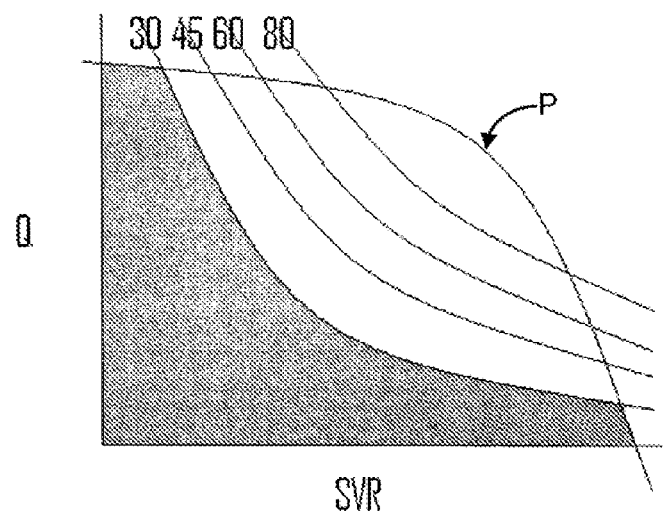
FIG. 4 is an isobar nomogram showing (i) a 'drop off zone' in the shaded area; and (ii) a region in which all actual physiological data compatible with life occurs.

As discussed above, it is accepted that the typical intrinsic resistance of the capillary beds requires a minimum pressure gradient of 30 mmHg to sustain flow; below this value circulatory arrest occurs. Accordingly, for the representation in FIGS. 3a-c the zone below a SPP of 30 mmHg can be identified to indicate an area in the visual representation which is not compatible with survival. This is shown as a shaded region in the isobar nomogram of FIG. 4. If data representing haemodynamic variables obtained from the subject trend toward the shaded zone it is immediately obvious that the subject is experiencing non-optimal haemodynamic performance. Once the subject's data enters the shaded region of the visual representation, the haemodynamic performance is no longer compatible with life.

In addition, the asymptote of the 30 mmHg isobar on the x-axis occurs at SVR of about 5 mmHg/l/min (or 400 SI units). By mapping data from patients undergoing anaesthesia or intensive care, it becomes apparent that for any particular SPP, all physiological data occurs in the area between the continuity of the curve P and the shaded area. Further, it has become apparent that patients whose haemodynamic data falls between the 30 mmHg and 45 mmHg isobars are likely to experience organ failure, and patients whose haemodynamic data falls within the 45 mmHg and 60 mm Hg isobars are likely to experience organ dysfunction.

By applying the principles discussed above, if any 2 of the variables related by Ohm's law as it relates to the systemic circulation are mapped on a graph, the value of the third variable can be read immediately from the mapping. Preferably, determination of the third variable is assisted by inclusion of markers (iso-flow lines, iso-resistance lines, isobars) representing a scale for the third variable according to the relationship SPP=CO×SVR. By generating a mapping which represents visually this relationship between the three haemodynamic variables, physicians are given a visual overview of circulatory function which enables them to determine and quantify haemodynamic performance at a glance and to direct therapy toward restoring optimal performance. This representation may be referred to herein as "haemodynamic mapping".

Of the various formats of haemodynamic mapping available, the mapping (graph) can be described in terms of the third variable. For example, a pressure-resistance graph can be described as an isoflow nomogram; a pressure-flow graph can be described as an iso-resistance nomogram; and a flow-resistance graph can be described as an isobar nomogram. Each case refers to the markers within the graph showing scale values for the third variable.

Some theories suggest that sepsis gives rise to the existence of a hypothetical "oxygen debt", if such a thing exists a method has not been found for quantifying it. More importantly, there is no existing method for calculating the cardiac output deficit which must be rectified to repay the debt and restore optimal haemodynamic function. This is of concern since these hypothetical deficits have been dealt with in the clinical environment by the application of principles based on out dated and unsupported circulatory models and guesswork.

The present invention provides a system for evaluating haemodynamic function in a human or animal subject or in a group of subjects. The system includes one or more transducers for monitoring continuously over time, either directly or indirectly, haemodynamic variables of the subject selected from the group comprising Systemic Perfusion Pressure (SPP), Systemic Vascular Resistance (SVR), and Cardiac Output (CO), and generating one or more corresponding data signals. Heart Rate (HR) and Stroke Volume (SV) may also be monitored. A processor receives the one or more data signals and generates a display signal for a visual representation of the data in which two of the variables are mapped in an x-y mapping according to the relationship SPP=CO×SVR. A display device receives the display signal and generates the visual representation, preferably in the form of a graphical mapping of the variables, wherein haemodynamic performance is determinable upon inspection of the visual representation.

Figure 5:
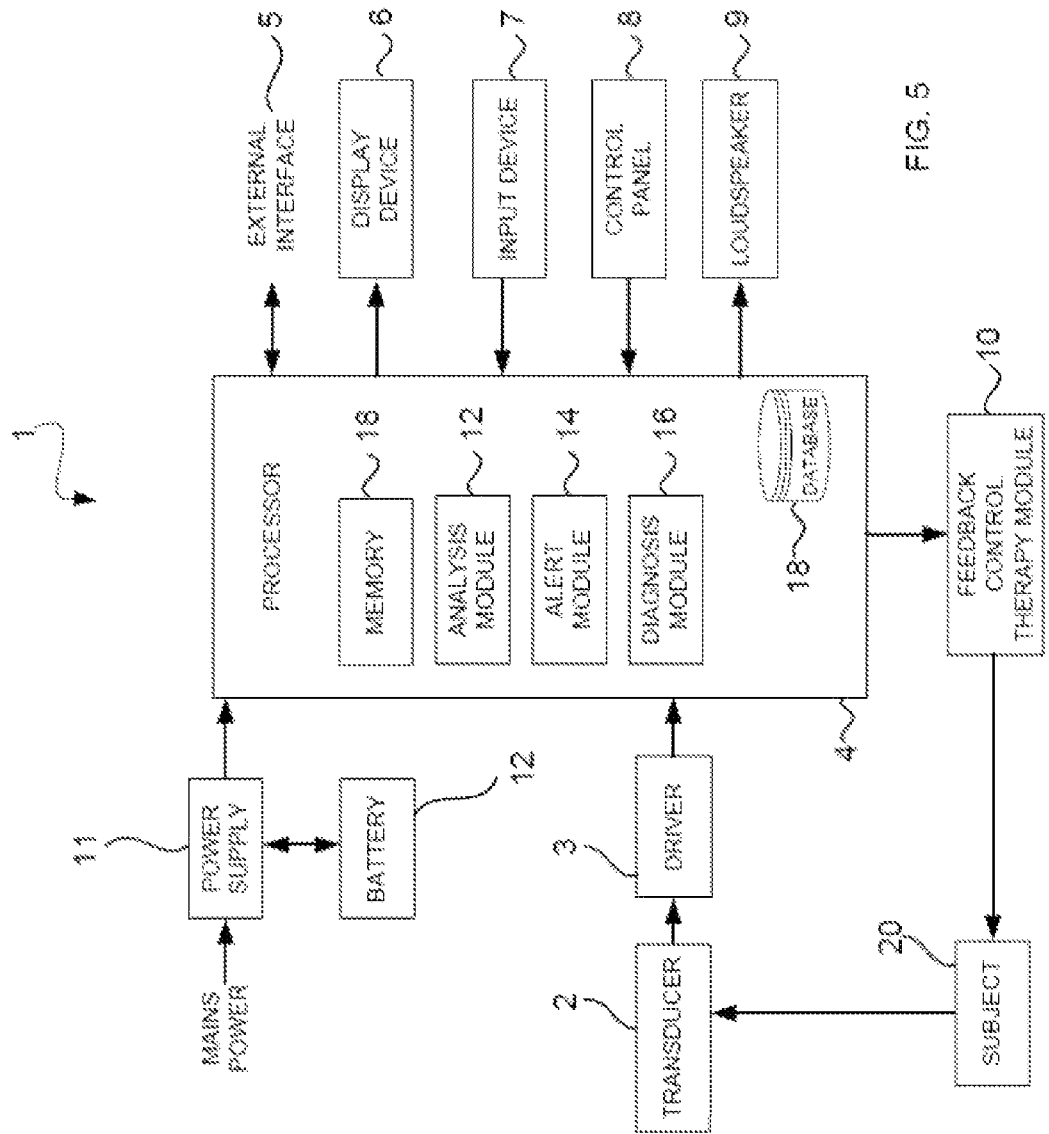
FIG. 5 is a functional block diagram showing components of a system according to an embodiment of the invention.

FIG. 5 provides a functional block diagram showing components of a system 1 for determining haemodynamic function in a human or animal subject according to an embodiment of the invention. The system, generally indicated by reference numeral 1 comprises one or more transducers 2 for monitoring physiological parameters which facilitate the determination of two haemodynamic variables in the subject selected from Systemic Perfusion Pressure (SPP), Systemic Vascular Resistance (SVR) and Cardiac Output (CO).

Data representing the two variables may be obtained using any suitable transducer or sensor. Typically the two variables are SPP (derived indirectly by monitoring MAP and CVP and calculating the difference) and CO. Preferably, the data set used to generate the visual representation is a substantially continuous dataset and the visual representation is generated in real time, although as an alternative the data may be collected and then processed at a later stage to generate the visual representation. Where the data is collected continuously and used in real time to generate the visual representation of haemodynamic performance, it is possible to monitor trends and changes in the subject's circulatory function in a manner which is more effective and accurate than the currently relied upon methods which involve monitoring a number of separate physiological parameters which, when taken on their own, do not provide any overview as to the haemodynamic performance of the subject.

The pulmonary artery catheter has an established role in determining flows and pressures within the circulatory system and has dominated the clinical environment. Not surprisingly however, the well documented morbidity and mortality accompanying its use continue to shrink its role in medicine. It is possible to measure haemodynamic parameters with less invasion than the pulmonary artery catheter. Some studies comparing different devices operating as cardiac output monitors suggest that most are reliable and yield values within about 10% of each other. Conversely, some devices, particularly those based on ultrasound techniques, require considerable familiarity for ideal data to be obtained and lose reliability with patient movement.

In a preferred embodiment, a device capable of providing a continuous data stream representing two of the three variables which can reliably indicate haemodynamic function in a subject is preferred. One such device was released by Edwards Lifesciences in 2005 for use with the "Vigileo" monitor. The Vigileo device relies on arterial pulse contour analysis and, when combined with a measurement of central venous pressure, is able to provide a continuous data stream of variables similar to those provided by a pulmonary artery catheter, namely CO and SVR. The Vigileo device also measures other parameters such as Stroke Volume, Stroke Volume Variation and mixed venous oxygen tension These variables provide useful supplementary information to physicians which may complement the inventive methodology. Alternatively, a pulmonary artery catheter or various other transducer devices may be used, as would be known to a person skilled in the art.

Transducers 2 are typically affixed to the appropriate body part of the subject 20 so as to obtain a sufficiently accurate and robust signal. A transducer driver 3 may be employed receive the signals from each transducer and condition the signal for input to the processor. Processor 4 receives the signals from driver 3 and processes them to generate a display signal. This is in turn used by display device 6 to provide a visual representation of the data. Typically the data is mapped or plotted with the two variables represented on an x and a y axis of the representation respectively. Processor 4 may also be provided with various modules such as an analysis module 12, an alert module 14 and a diagnosis module 16 and memory 18 (see below). Modules 12-16 may be provided integral with processor 4 or may be provided as external processors to improve system performance.

An analysis module 12 may be provided which approximates the autoregulation zone unique to the subject. This curve may be based on data received from the subject during normal health, while at rest. This data is then used to establish the subject's set point or zone for autoregulation and toward which therapy may be directed during e.g. anaesthesia. Alternatively, the autoregulation zone/set point may be determined by reference to pooled data from a group of representative subjects. In this case, the autoregulation zone/set point will not be specific to the subject being monitored but may be used, never the less to identify haemodynamic performance trends and non-optimal haemodynamic function in the subject, to approximate deficits in haemodynamic variables, and to optimise real time therapy.

The analysis module preferably identifies trends in subject data which indicate when the haemodynamic performance is non-optimal or becoming non-optimal. The analysis module may also be configured to identify a deficit in one or more of CO, SVR or SPP deficit and preferably communicate via alert module 14 that the subject requires therapy.

The analysis module may comprise an evaluation module for evaluating the effectiveness of a therapy (such as a drug or fluid administration) on an individual, or to evaluate the effectiveness of a therapy on a population of individuals (e.g. the elderly or more specifically, elderly females). This evaluation becomes particularly powerful when haemodynamic mapping is adjusted for HR as the actual effect of the therapy on the circulation can be determined without being masked by the compensatory effect of HR variation. The evaluation module may evaluate trends at a shorter time scale (i.e. micro trends) by identifying patterns in data occurring over windows several seconds or several minutes in duration. Alternatively/additionally, the evaluation module may evaluate trends at a longer time scale (i.e. macro trends) as may occur over several hours or days.

The alert module may communicate an alert by a message on display device 6 and/or loudspeaker 9. The deficit may be determined e.g. by reference to an autoregulation zone or set point unique to the subject or by reference to an autoregulation zone/set point representative of a population of healthy individuals or by extrapolating data values to a point of intersection representing a notional autoregulation zone unique to the subject.

A diagnosis module 16 may operate within processor 4 or may be a separate processor executing instructions which identify in the subject's data one or more patterns associated with a physiological syndrome. One physiological syndrome is heart failure. Haemodynamic mapping can be used to identify patterns indicative of early heart failure well before traditional indicators such as skin colour, perspiration and heart rate, lead to such a diagnosis. By identifying the syndrome earlier, therapies can be commenced immediately which lead to restoration of optimal or at least improved haemodynamic performance, and avoidance or organ damage.

Another identifiable physiological syndrome is shock. FIGS. 6a to 6d, 7a to 7d and 8a to 8d provide graphical representations of the types of patterns which may be used by a diagnosis module to stratify patient data into one of three shock "types". Although these figures show the shock pattern as a broken line, it is to be understood that the line is a guide only and that the diagnosis module is preferably configured to identify trends in the data (evident by changes in the variables over time) toward a particular shock pattern, rather than merely rely on the presence of data points appearing along the broken line to provide a determination that the subject is experiencing a particular shock type.

Preferably the diagnosis module is configured to make a determination about a subject's haemodynamic performance trending toward a single shock profile or a combination of two or more shock types. Other physiological syndromes or risk factors which may be identified by the diagnosis module include deep vein thrombosis and pulmonary embolism arising from low vascular flow identifiable in the visual representation or the data from which the mapping is constructed.

In a preferred embodiment, the diagnosis module 16 is configured to use the autoregulation zone and/or set point determined by the analysis module 12 recommended action for restoring optimal haemodynamic performance in the subject. The recommended action may involve a display of a message or alert that the subject is experiencing CO deficit and indicate that this should be rectified. Alternatively/additionally, the diagnosis module may, by reference to a database 18 or lookup table within the module, make a recommendation for therapy. This may include a recommendation for pharmacological intervention, fluid administration or the like.

A feedback control therapy module 10 may be provided which controls delivery or titration of therapy (e.g. drugs, oxygen, fluids etc) to the subject 20 directly via a therapy set such as a pump and catheter, face mask, nasal cannulae and the like. The feedback control therapy module is envisaged to automate titration of drugs or other therapy to a patient to achieve a desired SPP which may be established according to the individual's dose-response relationship for a particular drug, as may be determined by the analysis module. However it is envisaged that ultimate control will still rest with a physician who may override therapies determined by the diagnosis module and administered to the subject by the feedback control therapy module, therapy titration module or the like.

External interface 5 may additionally/alternatively be used to interface with external devices such as printers and network components. An input device 7 such as a keypad/mouse is preferably provided together with control panel 8, loudspeaker 9 and feedback control therapy module 10. The system may be powered by mains power through power supply regulator 11. In case of failure of mains power, a battery back-up 12 may be provided to ensure uninterrupted supply of power to the system.

Processor 4 preferably includes memory 18 storing computer processor executable instructions for performing the method according to the invention. The instructions may be installed in the memory by use of a software product or the like. The software product may be installed in permanent memory of the processor such as may be the case in a proprietary system sold with the software application pre-installed. Alternatively, the software application may be installed on an existing computing device (such as a Vigileo or other monitor as may be used in the clinical environment) using a software product purchased on a disc or other storage device or downloaded via a network connection or the like.

For a subject in whom haemodynamic performance is being determined, a series of values obtained from the subject over time is used to generate the visual representation. Values obtained from a subject at rest and in a generally healthy state may be sufficiently stable that they become representative of the subject's unique autoregulation zone. This can be represented in various formats. From these formats it is possible to ascertain the subject's autoregulation zone or a "set point" at which optimal haemodynamic performance occurs. Example 7 provides haemodynamic mappings obtained from an actual subject according to embodiments of the invention in which autoregulation data is mapped to provide visual representations of haemodynamic function for a 94 year old woman.

The accuracy of the haemodynamic mapping may be improved by providing a correction to account for the influence of vessel contractility/elastance (inverse of compliance) on the SPP and the SVR. Equation 1 provides SPP=CO×SVR where SVR is provided in mmHg/L/min. It is noted that:

$$CO = HR \times SV \quad \text{(Equation 4)}$$

However, substituting Equation 4 into Equation 1 gives:

$$SPP = HR \times SV \times SVR \quad \text{(Equation 5)}$$

which is in units of beats·mmHg. This indicates that actual measurements of SPP (more specifically, SVR which is a determiner of SPP) requires a correction for HR to give a fuller picture. Thus, a correction may be made by correcting SVR for variations with each contraction of the left ventricle. A corrected SVR may be referred to as actual Systemic Vascular Resistance (aSVR) per beat, where:

$$aSVR = SVR \times HR \quad \text{(Equation 6)}$$

Which can be rearranged to give:

$$SVR = \frac{aSVR}{HR}$$

This yields the following relationship:

$$SPP = SV \times aSVR \quad \text{(Equation 7)}$$

where aSVR is an indicator of the resistance to blood flow, presented by the vasculature (in mmHg/L), per contraction of the left ventricle. aSVR is influenced by the ability of the vasculature to recoil after each ventricular contraction and is therefore an indicator of the elastance of the circulation. Utilising aSVR instead of SVR corrects a flaw in the existing understanding of the circulation and a haemodynamic mapping plotting values of SV against aSVR enables physicians to investigate drug effects on the vasculature more effectively because the extraneous influence of haemostatic adjustments of HR on e.g. SPP or traditional SVR, are eliminated. Case Studies 1 to 4 demonstrate benefits associated with correcting for HR when performing haemodynamic mapping according to embodiments of the invention.

These observations highlight the possibility that the currently understood adrenoceptor selectivity associated with inotropic drugs may not apply equally to all subjects. When the effect of HR is accounted for, the effects of adrenaline, noradrenaline and metaraminol appear to be substantially identical. This leads to the possibility that e.g. the principal determinants of whether these drugs change peripheral vascular tone could be age and gender. For instance, it could be that in the premenopausal circulation, these agents all act as inotropes, but have different chronotropic activity (adrenaline increases HR; noradrenaline and metaraminol decrease HR) whereas in the post-menopausal circulation the dominant effect is on the peripheral vascular muscle, since the heart becomes stiff with age and SV fixed.

Furthermore, the inventor of the present invention hypothesises that there are three discrete patterns in the circulation. When one pattern resolves and a different pattern develops, the pressure at which the pattern changes is the lower inflection point of the autoregulation zone. That is, the lower inflection point is the point or region around which these patterns 'rotate'.

In a preferred embodiment, the method includes identifying in the subject's data as mapped in the visual representation one or more patterns associated with a physiological syndrome such as shock. By using the inventive method to generate visual representations of haemodynamic performance for a range of subjects, the inventor has observed three distinct patterns of shock (low blood pressure) as follows.

In the first pattern, labelled herein as Type 1 shock, the subject experiences decreasing SVR and compensatory increases in CO to maintain substantially stable SPP, even though there may be severe pathology. Type 1 shock is observable in clinical situations including but not limited to early sepsis, in the Systemic Inflammatory Response Syndrome (SIRS), trauma and pancreatitis. It is hypothesised that circulatory failure (i.e. failure of the vascular pump) followed by compensation by the cardiac pump is the aetiology underlying Type 1 shock. Type 1 shock is a normal response, but where compensation is incomplete, the pressure gradient will trend across isobars toward the lower inflection point. Even though flow is relatively increased, in Type 1 shock this flow is insufficient to maintain a normal organ perfusion pressure, and organ dysfunction will ensue. Case Study 5 relates to compensatory shock of the kind referred to as Type 1.

In the second pattern, labelled herein as Type 2 shock, the subject experiences decreasing SVR and SPP while maintaining substantially stable CO. Type 2 shock is observable in clinical situations including but not limited to diastolic dysfunction, multiple organ dysfunction syndrome, late sepsis and acute myocardial infarction. It is commonly observed in the elderly (particularly elderly females) due to the widespread phenomenon of diastolic dysfunction after menopause in which there is little variability in SV and CO is therefore increased only be increasing HR (an inefficient means to increase CO). It is hypothesised that circulatory failure (i.e. failure of the vascular pump) and failure of the cardiac pump is the aetiology underlying Type 2 shock. Case Study 6 relates to Type 2 shock.

The third pattern, labelled herein as Type 3 shock sees the subject experience decreasing CO and SPP but substantially no change in SVR. Clinical situations in which Type 3 shock is observable include anaesthesia, haemorrhage, cardiogenic shock (significant loss of cardiac muscle mass) and cardiogenic pulmonary oedema, LV infarction, hypovolaemic shock, and possibly Addisonian shock, since there is hypotension resulting from adrenal failure and the adrenal is an important component in the neuro-endocrine regulation of pressure, flow and resistance. This shock pattern is uncommon in anaesthesia and intensive care, where Type 1 is predominant in 'flow-dependent pressure regulators' and Type 2 is predominant in elderly 'resistance dependent pressure regulators'. It is hypothesised that pure cardiac failure gives rise to Type 3 shock.

Unlike the Rivers' Protocol, the present invention provides a means to distinguish physiologically discrete subgroups with sepsis. Thus, by monitoring CO, SVR and SPP (i.e. MAP-CVP) and observing, using haemodynamic mapping, patterns of change in these parameters (or e.g. in SV and aSVR), a patient can be stratified as a Type 1, 2 or 3 pattern, referenced to normal values for the age and gender of the patient, and therapy can be guided accordingly.

The characteristics of the three patterns of shock are summarised in FIG. 31. Each of the shock syndromes, can be represented visually and in a range of different graphical formats such as for example:
- a Pressure-Flow mapping;
- a Pressure-Resistance mapping; and
- a Resistance-Flow mapping.

In each case, according to embodiments of the invention, data obtained from the subject which, on visual inspection, trends toward a pattern indicative of a shock syndrome, can be used to direct therapy.

Figure 6A:
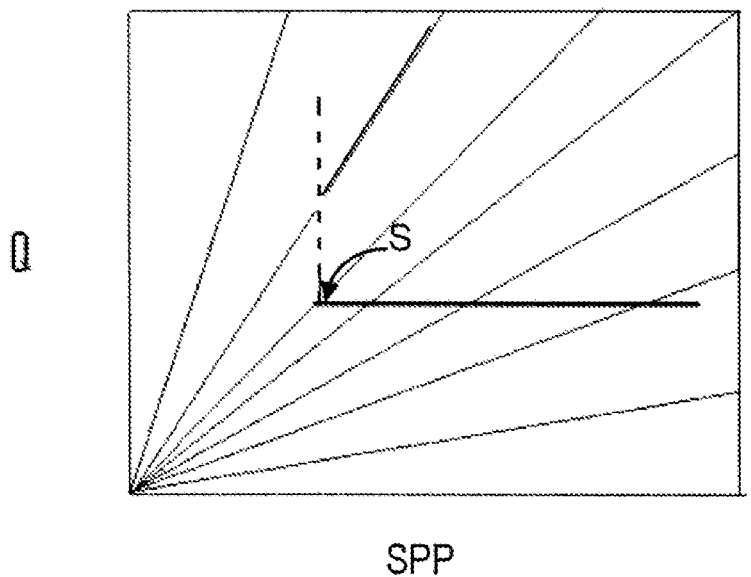
FIGS. 6a to 6d correspond to one format of visual representation in which data may be mapped on a pressure-flow graph.
Figure 6B:
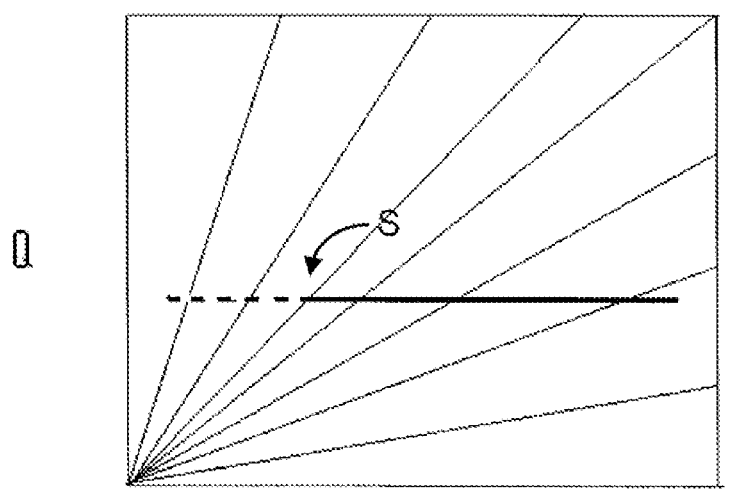
Figure 6C:
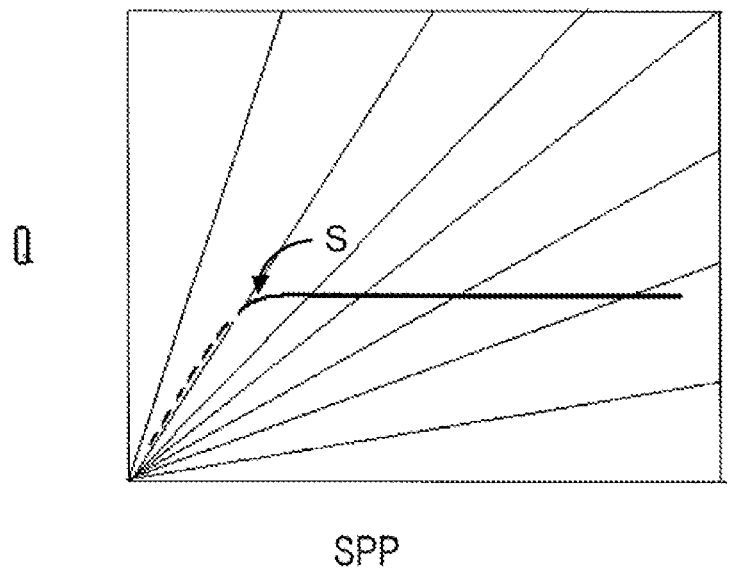
Figure 6D:
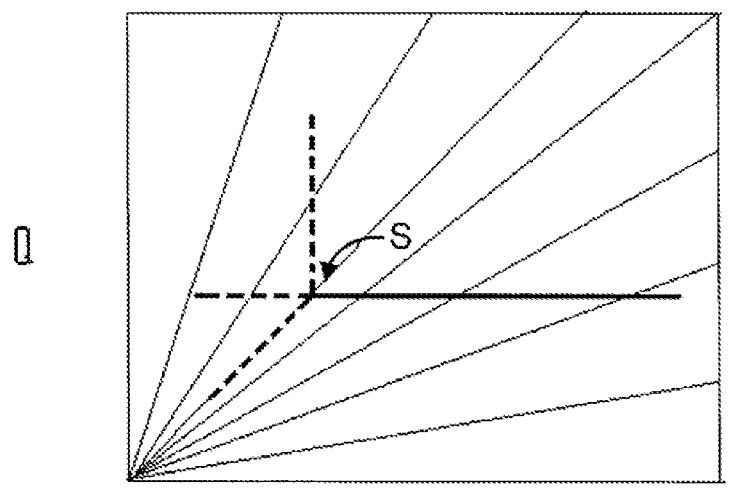

FIGS. 6a to 6c represent pressure-flow curves corresponding to the patterns of each of the three shock syndromes. The broken line represents the trend observable, moving away from the set point S, when the subject's haemodynamic performance becomes sub-optimal and trends toward one of the shock states. In each representation, the solid line represents a range optimal haemodynamic performance. FIG. 6a shows Type 1 shock, FIG. 6b shows Type 2 shock and FIG. 6b shows Type 3 shock patterns. The markers radiating from the origin represent a scale for SVR, increasing in value from left to right. Each scale marker is referred to as an "iso-resistance" line. FIG. 6d represents the aggregation of patterns in FIGS. 6a-6c in which all three shock states are represented by broken lines.

Haemodynamic mapping of large volumes of data for groups of subjects can be used to establish values or ranges of values for CO, SVR, aSVR and SPP that are normal for age and gender. This provides a useful starting point for therapy in shock states. The ideal situation is to have pre-morbid (pre-induction) data for the individual before shock states develop (Case Study 6), but in the absence of this information (Case Study 5) there is sufficient agreement across a groups of like patients that pooled data can usefully guide treatment.

Interestingly, although the generic autoregulation curve is often shown with the pressure and flow decreasing to zero, as has been discussed, the intrinsic resistance of the capillary beds leads to an abrupt cessation of flow at a perfusion pressure gradient of 30 mmHg in the 'normal' subject. In pure heart failure, the pressure and flow decrease below the set point S along an "iso-resistance" line which terminates at a discrete point that typically corresponding to a SPP (i.e. a gradient) of 30 mmHg. This has not been recognised previously.

In the subject with hypertension whose autoregulation zone is at a higher perfusion pressure, the gradient of the curve below the lower inflection point is less because the subject's cardiac output decreases along a different iso-resistance line. This is not observed in the Guyton model because it does not recognise that the iso-resistance line (and in fact the autoregulation curve) is specific to the haemodynamic performance of the individual. In circulatory failure with systolic dysfunction (e.g. dilated cardiomyopathy) the subject's haemodynamic mapping shows a trend somewhere between the patterns representing Type 1 and Type 2 shock, since cardiac compensation is incomplete. In late sepsis, the heart becomes involved in the process, and is no longer able to compensate for the failure of the vascular pump. Thus the Type 2 pattern dominates in data corresponding to the inflammatory response with cardiac involvement.

Figure 7A:
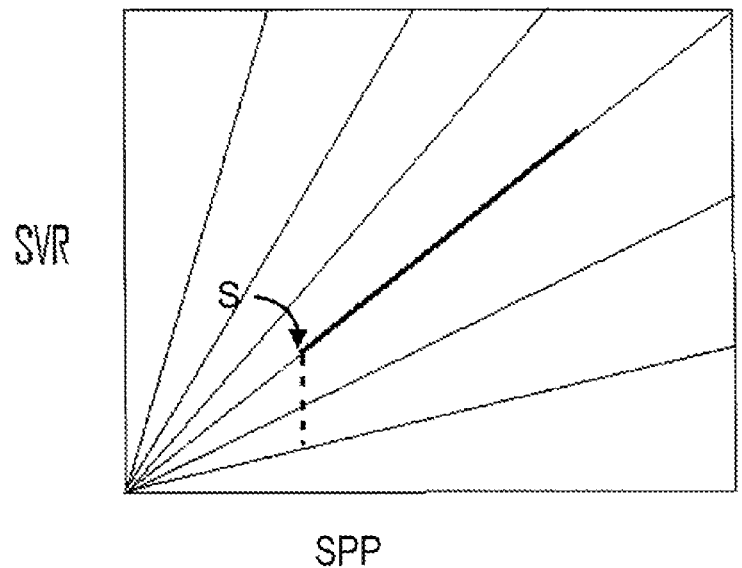
FIGS. 7a to 7d correspond to an alternative format of visual representation in which data may be mapped on a pressure-resistance graph.
Figure 7B:
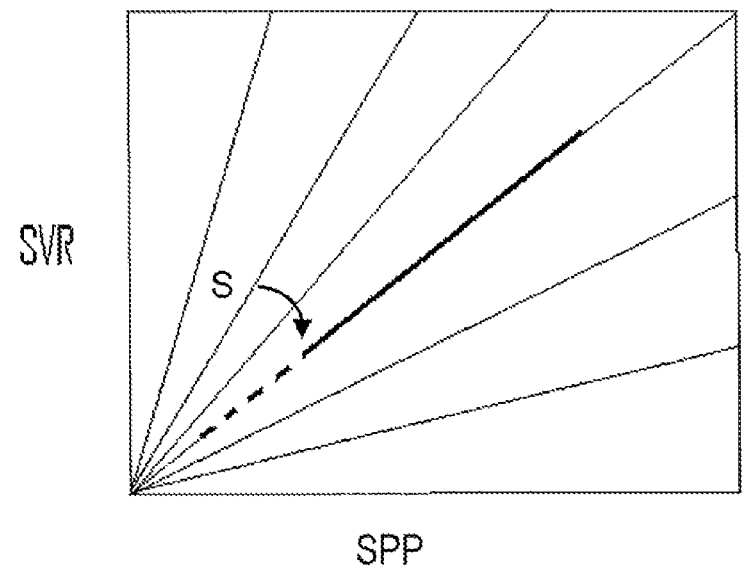
Figure 7C:
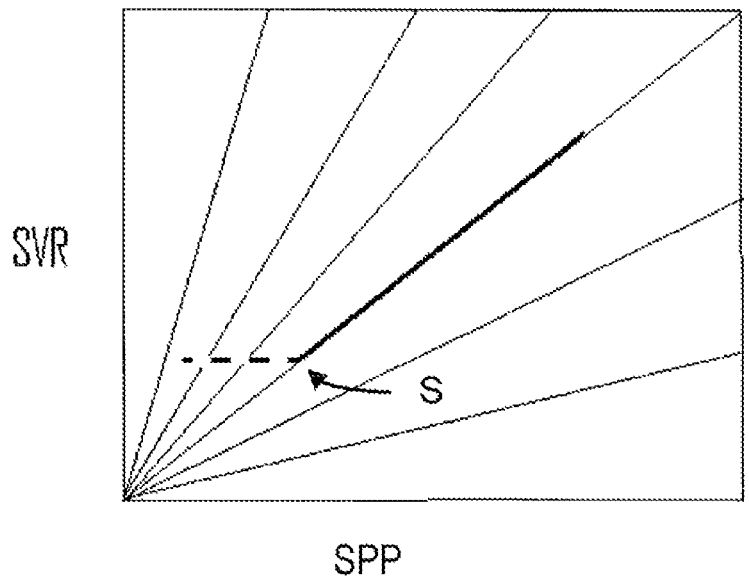
Figure 7D:
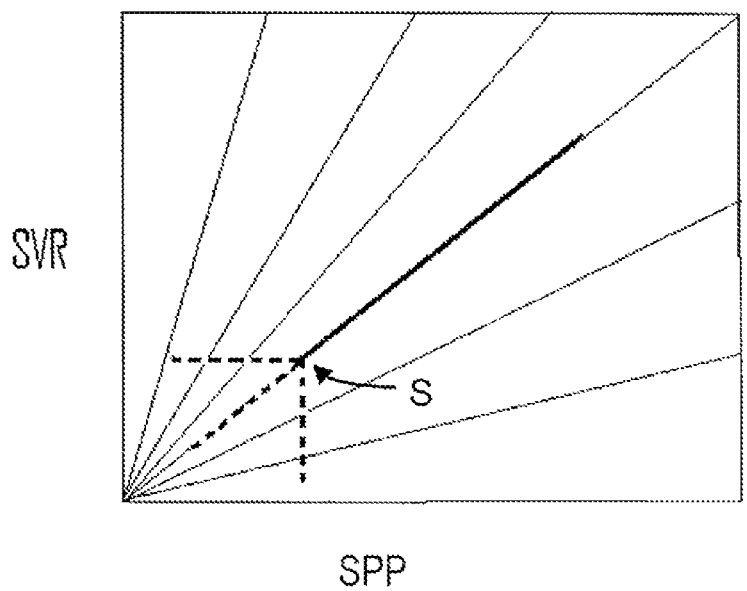

FIGS. 7a to 7c represent pressure-resistance curves as an alternative approach to visual representation of the haemodynamic performance of a subject and in which patterns of shock can be identified. Here, the subject's resistance values (SVR) are plotted on the y-axis against pressure (SPP) on the x-axis. The broken line in each case represents the trend observable, moving away from the set point S, when the subject's haemodynamic performance becomes sub-optimal and trends toward one of the shock states. In each representation, the solid line represents a region of optimal haemodynamic performance, i.e. the autoregulation zone. The lines radiating from the origin represent a scale for CO, increasing in flow rate from left to right. Each scale marker is referred to as an "iso-flow" line. FIG. 7a shows Type 1 shock, FIG. 7b shows Type 2 shock and FIG. 7c shows Type 3 shock patterns. FIG. 7d represents the aggregation of patterns in FIGS. 7a-7c in which all three shock states are represented by broken lines.

Figure 8A:
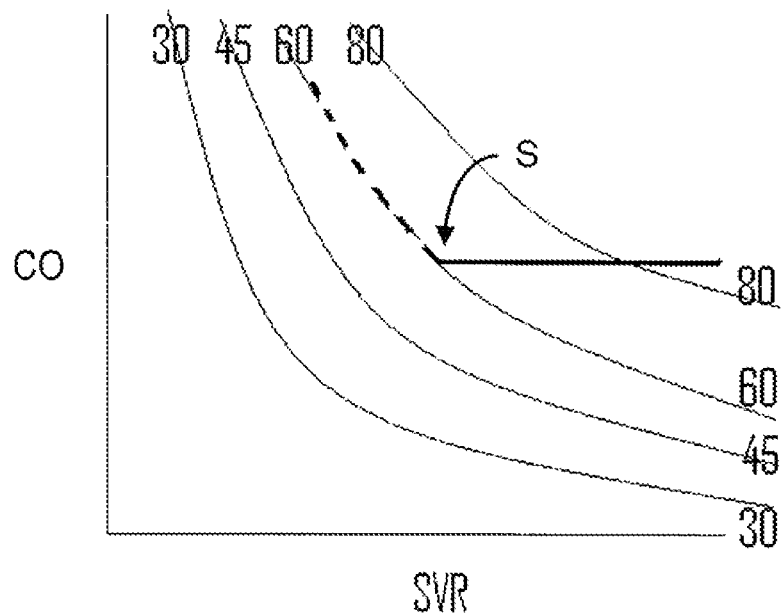
FIGS. 8a to 8d correspond to yet another format of visual representation in which data may be mapped on a resistance-flow graph.
Figure 8B:
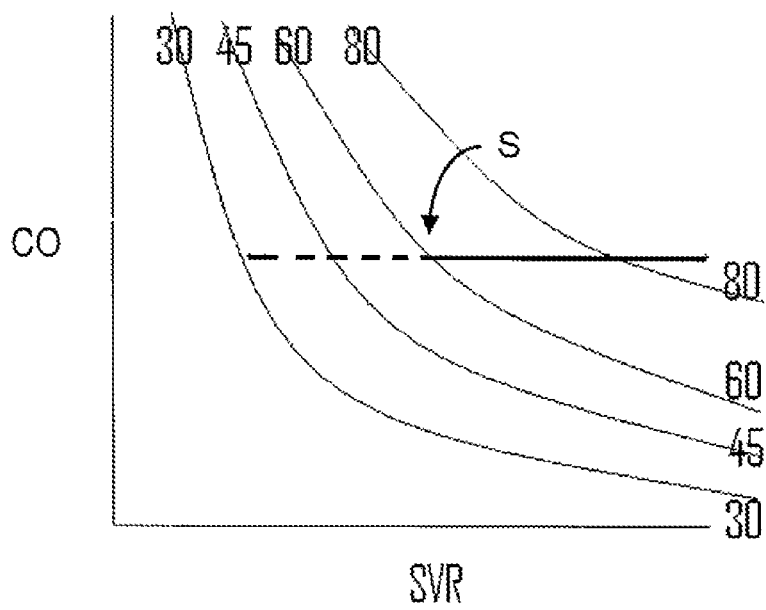
Figure 8C:
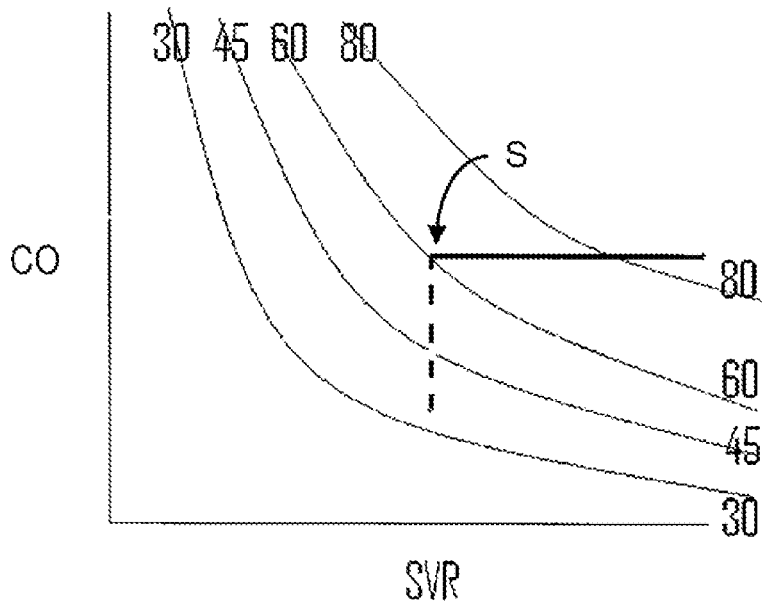

FIGS. 8a to 8c represent resistance-flow curves as another alternative approach to visual representation of the haemodynamic performance of a subject in which patterns of shock can be identified. Here, flow (CO) is plotted on the y-axis against resistance (SVR) on the x-axis. The broken line in each case represents the trend observable, moving away from the set point S, when the subject's haemodynamic performance becomes sub-optimal and trends toward one of the shock states. Again, the solid line represents a region of optimal haemodynamic performance, i.e. the autoregulation zone. The markers in the form of isobars represent a scale for SPP. This representation is arguably the most useful in the clinical setting as it provides an immediate visual representation of when the subject's haemodynamic variables are approaching the "drop off zone", i.e. a perfusion pressure gradient less than 30 mmHg and insufficient to sustain flow to all organs.

The resistance-flow representation yields information which is useful for tracking the subject's response to treatment, as well as permitting diagnosis of shock patterns. The shock pattern indicated in FIG. 8a is representative of Type 1 shock and is seen in early sepsis and SIRS. Because of the function of baroreceptors, presumably in the carotid sinus, the body attempts to maintain the systemic perfusion pressure in the autoregulation range, i.e. along the isobar corresponding to the autoregulation zone. When systolic function is impaired, the Type 1 pattern is still recognizable, and it is possible to identify a 'cardiac output deficit' which can readily be quantified. This is an improvement over the traditional model in which the deficit is a theoretical value to which the cardiac output is made to increase in order to achieve adequate oxygen delivery. Moreover, a 'resistance deficit' can be determined also. The goal of therapy, and the result of recovery, is to return the patient to the plateau of normal autoregulation.

CO deficit can be determined (and in some embodiments, quantified) in a number of ways. One method involves referring to haemodynamic variables obtained from the subject while functioning normally (i.e. at rest in a normal healthy state), or referring to the subject's unique autoregulation zone or predetermined "set point" for optimal haemodynamic performance. Since the pre-insult 'systemic perfusion pressure' is the minimum required for normal haemodynamic performance in the subject, when the SPP falls below this level, the subject is considered to be in a disease state and recovery is achieved by restoration of the normal SPP gradient. Thus, by identifying the 'set point' (e.g. measuring CO and SVR before an e.g. before commencement of anaesthesia) it becomes possible e.g. in the intensive care setting, when the pattern of response changes, to quantify the degree of the change (i.e. the deficit) in one or more of the variables.

If data corresponding to the subject's autoregulation zone (i.e. pre-insult haemodynamic data) is not available, it is possible to estimate the deficit in one or more of the haemodynamic variables by making assumptions about the typical subject and their haemodynamic profile during normal health while at rest. It is possible to apply the assumption that a person requires a minimum 'systemic perfusion pressure' gradient above of 30 mmHg to maintain systemic circulation. This rule may be altered according to health factors likely to affect the subject's normal haemodynamic function. For example, in the hypertensive subject the required SPP may be assumed to be 80 mmHg.

By graphing e.g., CO and SVR it becomes possible from the resulting 'isobar nomogram' to determine that the required minimum pressure can be reached by either increasing the CO (plotted from the y-axis) or by increasing the SVR (plotted from the x-axis). The amount of increase required is indicative of the deficit in the respective variable.

In a third method for quantifying the deficits, if the haemodynamic mapping pattern changes, it will be possible to identify by interpolation of available data to locate a 'crossover' at an inflection point which appears to be the 'set point' for the subject. This can be modified by drugs on the 'downward side' so that the subject appears to maintain a particular pressure by varying flow and resistance, but drugs appear to reset the 'set point' only where pressure is below the physiological level.

The shock pattern indicated in FIG. 8b is seen in late sepsis, MODS and diastolic dysfunction due to a range of cardiac diseases. Here, it is clear that both the vascular pump (i.e. the circulation) and the cardiac pump have failed, although it is not a pattern of systolic dysfunction.

The shock pattern indicated in FIG. 8c is seemingly prevalent in patients undergoing major surgery. Interestingly, although the variables in this pattern are within acceptable ranges based on traditional thinking and there is no "clinical" evidence of heart failure, the inventor has discovered through mapping actual patient data according to the invention, that it is possible to detect trends which lead to heart failure well before there are clinical signs of the shock syndrome. This becomes more evident in the examples which follow.

Figure 8D:
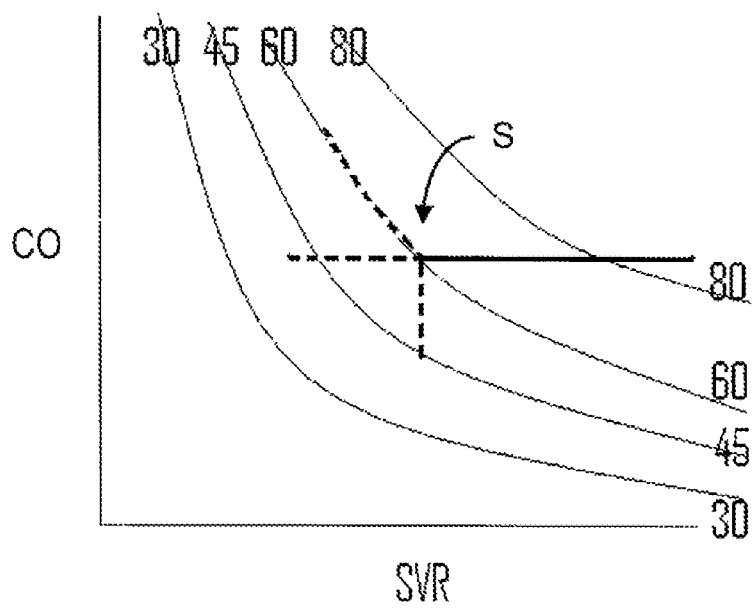

FIG. 8d represents the aggregation of patterns in FIGS. 8a-8c representing all three shock states represented by broken lines.

Using the trending information ascertainable from the graphical mapping of haemodynamic data obtained in accordance with the present invention, it is quickly apparent whether a subject is or approaching a Type 1, 2 or 3 pattern of shock or a combination of these, or some other syndrome. When the variables are mapped in real-time, the mapping also reflects changes in haemodynamic performance in response to therapy including administration of drugs. Because micro trending reflects immediately the action of any drug which has been administered and acts on the heart or circulation, the mapping will identify subjects who are responders and non-responders to a treatment, so treatment can be quickly modified and titrated to achieve the best response possible. Thus, in the case of an inotrope such as noradrenaline, the existence of a response, the nature of the response and the rate and degree of the response become immediately evident. Moreover, the mapping technique makes it possible to map a dose-response relationship in an individual case to different doses of drug or a dose-response relationship in a population of individuals to different drugs and drug doses. The present invention makes it possible to "map" the instantaneous pattern of variation of pressure, flow and resistance in response to any drug in a sensitive manner that has not been possible with the previous techniques. This opens the door to personalised therapies, in anaesthesia and resuscitation.

This new paradigm for monitoring haemodynamic performance and for understanding the circulation according to the present invention creates benefits in understanding and treating many patients. Of particular interest is the septic patient who experiences an increase in metabolic demands which must be met by increased oxygen delivery to the tissues.

According to traditional principles, has long been accepted that in the septic patient, a situation akin to exercise physiology is present. In the maximally exercising subject, the cardiac output increases to a physiologic limit and if the rate of exercise is continued above this limit, an "oxygen debt" accrues. Continued exercise remains possible due to anaerobic metabolism and when exercise ceases, the cardiac output gradually returns to pre-exercise levels during which time the "oxygen debt" is repaid.

The analogy which is drawn between exercise and the septic patient having up-regulated CO to meet the increased metabolic demands created by e.g. bacterimia, has led to the description of sepsis as a "hyperdynamic state". In this state, the heart works to increase CO and hence oxygen delivery. Pharmacological methods of increasing CO, and of loading the blood with oxygen for acidotic tissues should therefore have a beneficial effect on organ function and mortality. This has been brought into effect in traditional practice by protocolizing oxygen delivery to increase cardiac output to a 'goal' of 4.5 l/min/m$^2$ per unit Body Surface Area (BSA); or aggressively fluid loading patients and giving inotropes according to the complicated algorithm of Rivers (NEJM, 2001). However, these approaches have enjoyed varied success which brings into doubt the effectiveness of current treatment protocols.

Referring to sepsis as a "hyperdynamic state" implies that increased cardiac effort is required to fight the infection (i.e. to achieve increased oxygen delivery to the affected tissue). However, using the visual mapping technique according to embodiments of the present invention, sepsis may now be explained by reference to bacterially induced circulatory failure based on the two pump model involving the cardiac pump and the vascular pump.

The implications for understanding and treating sepsis are great: in response to a loss of vasomotor tone in the circulation, the CO is increased by a feedback mechanism involving the baroreceptors in the circulation. If the MAP before sepsis is 5 L/min, with a SVR of 15 mmHg/L/min (i.e. 1200 dyne sec/cm$^5$ in SI units), and with onset of sepsis the SVR decreases to 7.5 mmHg/L/min (600 dyne sec/cm$^5$) but the CO increases to 10 L/min, then the power generation increases from 375 to 750. Thus, whereas sepsis has been labelled a "hyper-dynamic state" without really understanding why, it can now be explained by the necessary increase in power generation at rest in a patient with circulatory failure and increased CO.

As indicated in the foregoing, the Rivers' protocol formalizes goals for MAP (65 mm Hg) and CVP (10-12 mm Hg) which have broad support within clinical medicine. However, these targets have no correlation with pre-morbid healthy patients and there is no physiological model which supports these values as appropriate haemodynamic goals for management. Further, the goals do not discriminate between patient subgroups. Rather, they assume uniformity in haemodynamic performance among subjects irrespective of age, gender, lifestyle and the like.

Figure 16:
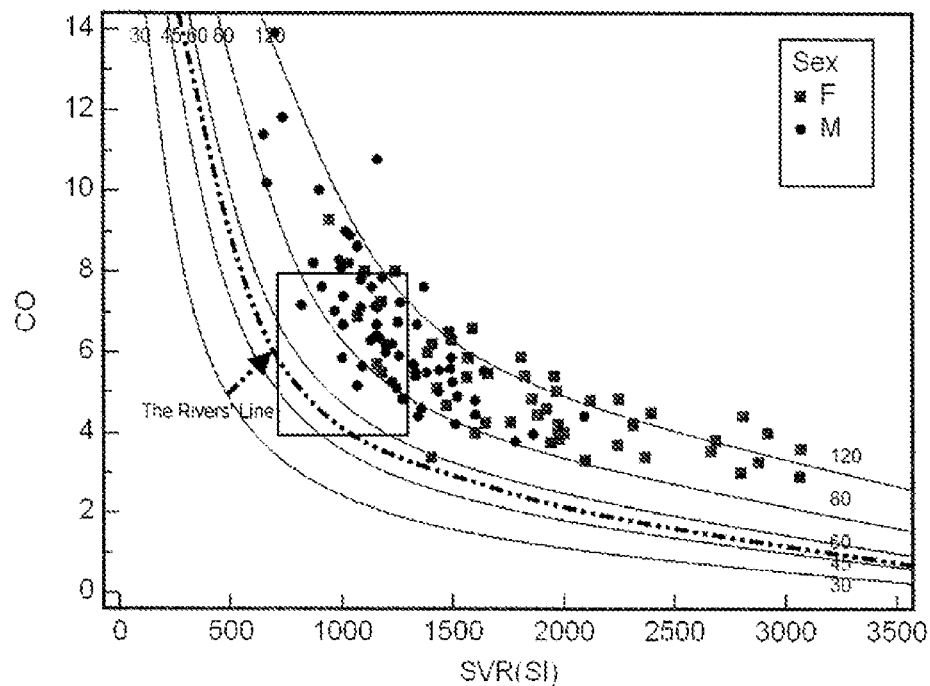
FIG. 16 presents SVR data for elderly male and female patients prior to induction of anaesthesia for major elective surgery.

With slight variation between different authorities, normal haemodynamic values are said to be represented by an SVR of 900 to 1400 dyne·sec/cm$^5$ (11.25 to 17.5 mmHg/L/min) and a Cardiac Output Index of 2.5 to 3.5. This roughly equates to an area described by a rectangle having CO bounds of 4 and 8 L/min and SVR limits of 900 to 1400 dyne·sec/cm$^5$. This rectangle is shown in FIG. 16 which presents actual haemodynamic data for elderly male and female patients prior to induction of anaesthesia for major elective surgery. When regarding these data it becomes apparent that very few female patients in this cohort are within "normal" parameters. Rather, approximately 1 in 20 elderly female patients, and about half of the elderly male subjects observed exhibit haemodynamic performance within "normal" ranges.

Analysis performed using the haemodynamic mapping techniques of the present invention has revealed profound ways in which the elderly male and female circulation differ. By mapping data obtained from elderly patients in accordance with embodiments of the present invention, it becomes apparent that there is a significant change in the way the heart and circulation work in advanced age, and a significant deviation occurs in typical haemodynamic values according to gender. Without this kind of subgroup analysis, the effect of traditional treatment regimes also likely to produce a mix of improved and worsened outcomes which obscure the actual effect of therapies administered.

Figure 17:
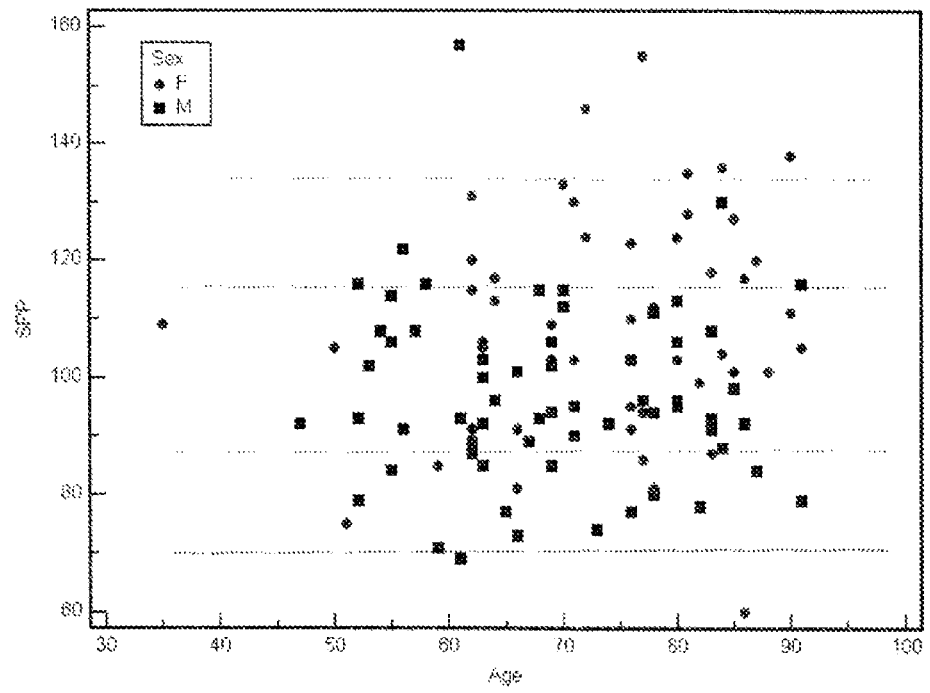
FIG. 17 presents SPP data for the same subjects represented in FIG. 16, graphed against age.

When SPP data from the same patients presented in FIG. 16 is graphed against age (FIG. 17) it becomes apparent that there is a gender-based difference in SPP; male patients are typically distributed between 70 and 115 mmHg whereas female patients are typically distributed between 90 and 130 mmHg. This fact alone is of interest since the incidence of coronary artery disease (CAD) in females reaches parity with men in the sixth decade. Since a MAP of 65 mmHg and CVP 10 to 12 mmHg equates to a SPP of 53 to 55 mmHg, it becomes obvious that there is not only a major deviation in the elderly from 'normal' values, but that there is significantly greater degree of hypertension in elderly female patients than elderly male patients.

Figure 18:
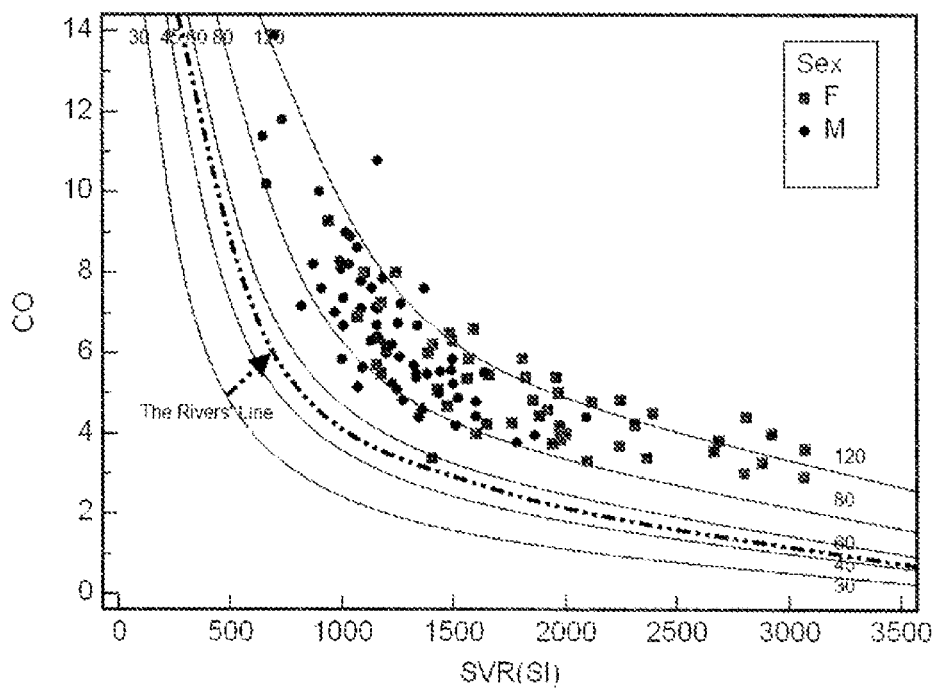
FIG. 18 is an isobar nomogram representing the male and female data from FIGS. 16 and 17.
Figure 19:
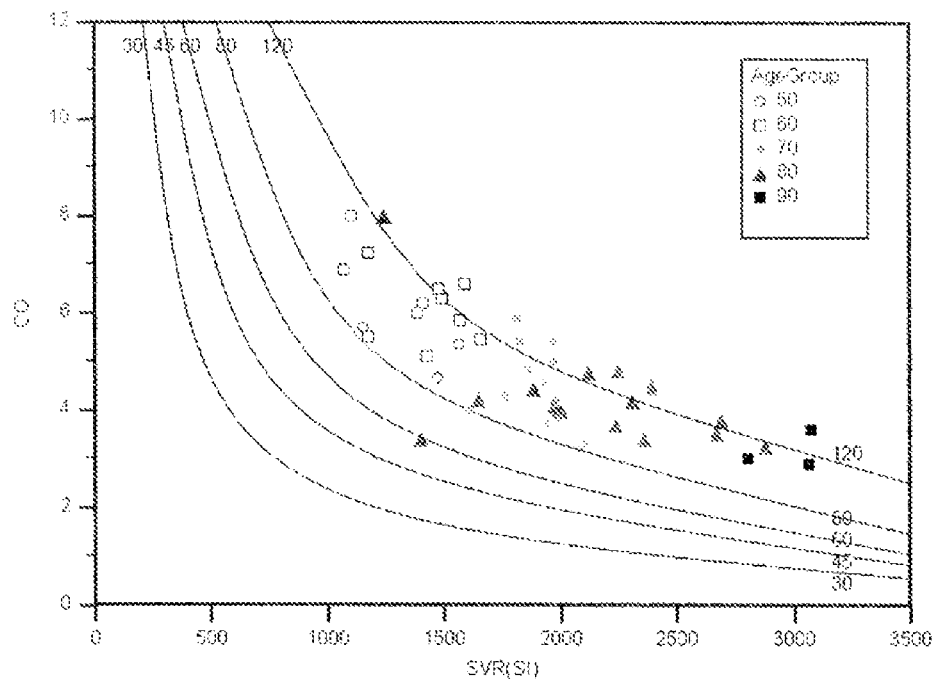
FIG. 19 is an isobar nomogram for 47 normal elderly female patients prior to induction of anaesthesia.

The physiological differences between elderly male and female patients are much greater than this suggests. The data from FIG. 17 are presented again in the isobar nomogram of FIG. 18 which shows that while male and female patients have similar perfusion pressures (between the 80 and 130 mmHg isobars) there is a considerable divergence of CO and SVR in the two gender groups. If the female patients are separately analysed, and subdivided according to age it can be seen that with advancing age, the CO at rest progressively falls, and the SVR at rest progressively rises. See for example FIG. 19 which plots data for 47 normal elderly female patients prior to induction of anaesthesia.

Employing the inventive techniques of haemodynamic mapping, it can be seen that from the age of 60 years onward, there is progressive deviation from haemodynamic parameters traditionally accepted to indicate "health" or normal haemodynamic performance. This may be considered to point to age-onset diastolic dysfunction.

Figure 20:
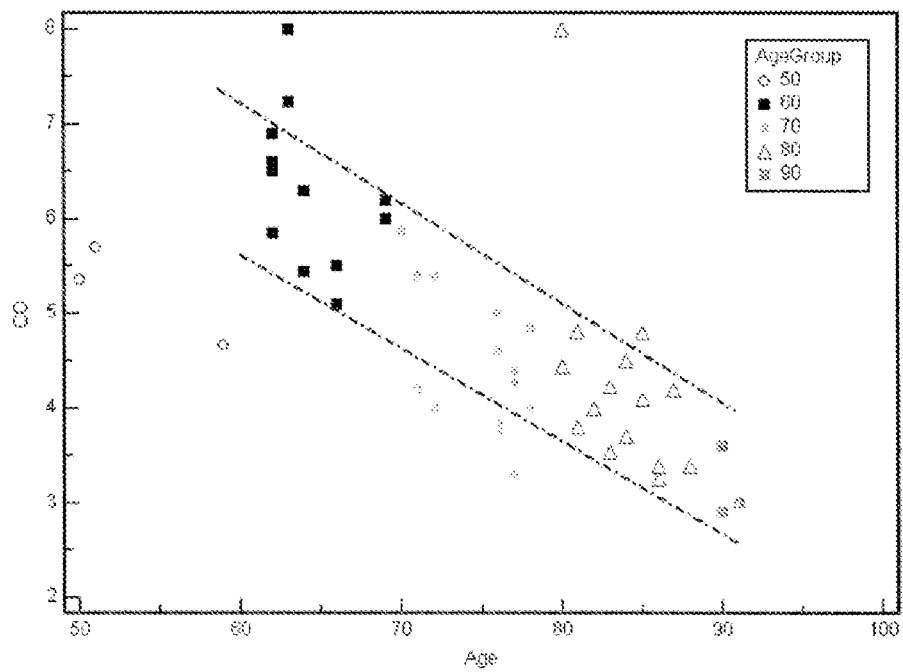
FIGS. 20 and 21 are plots showing the relationship between pre-induction CO and age for the 47 normal elderly female patients also plotted in FIG. 19.
Figure 21:
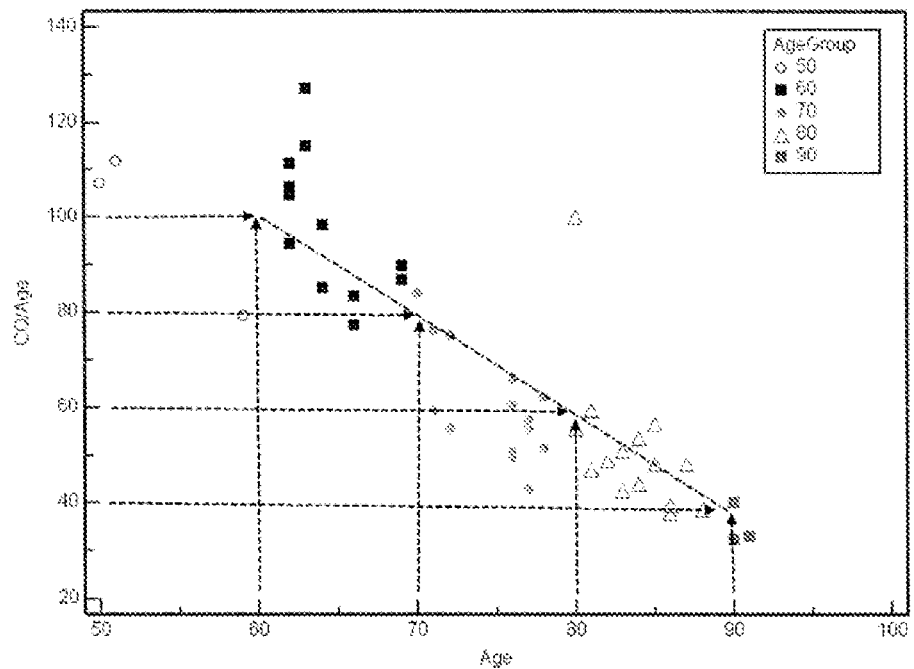

If pre-induction CO is graphed against age for the same 47 female subjects (FIG. 20), we see that CO in elderly females begins to fall from about the age of 60. Since the SPP must be maintained, it follows that SVR increases with advancing age. On the basis of the 47 female patients in this cohort, the inventor has devised a 'rule of thumb' method for estimating what the expected CO in an elderly female patient should be. This is demonstrated in the data presented in FIG. 21, which shows that the progressive fall in CO with age, and FIG. 32 which sets out the inventor's "60-70-80-90/100-80-60-40 rule for expected CO in elderly females.

Figure 22:
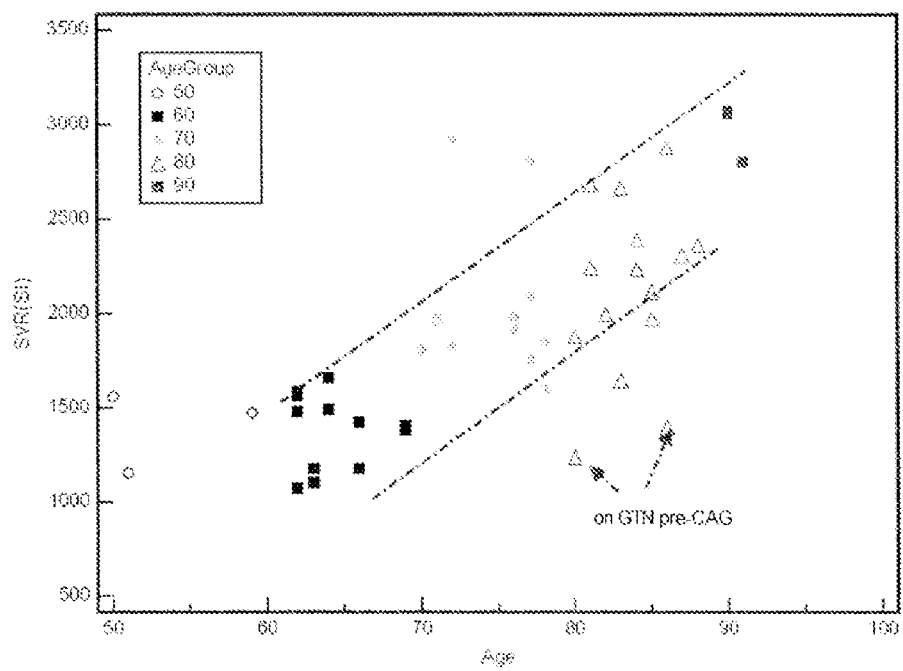
FIGS. 22 and 23 show age distribution of SVR in elderly females.
Figure 23:
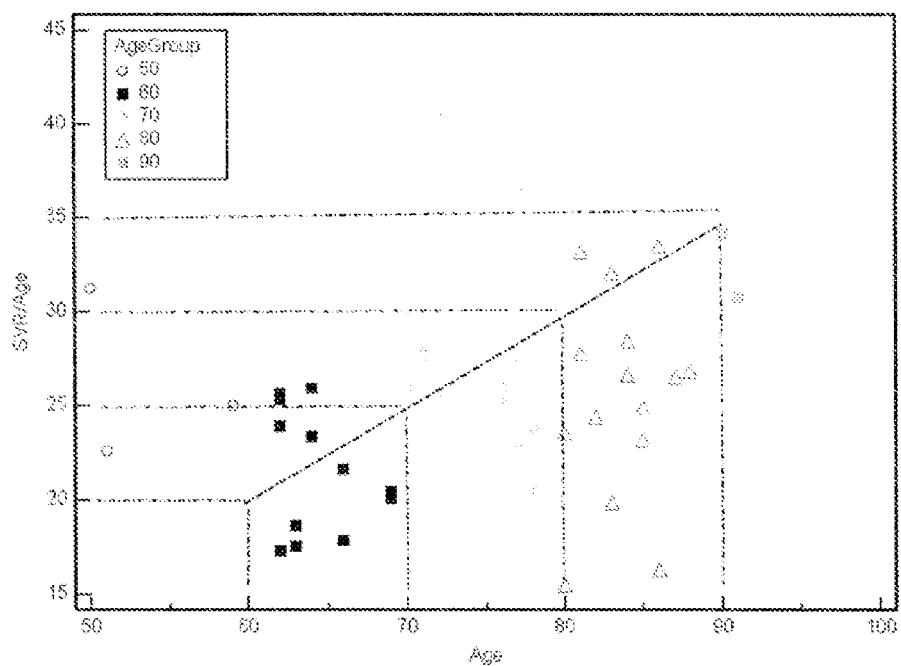

Although it is 'less neat' than the corresponding analysis for CO, a rough 'rule of thumb' method has also been devised for estimating rising SVR with age in the elderly female. This is based on mappings such as those illustrated in FIGS. 22 and 23. FIG. 33 sets out the inventor's 60-70-80-90/20-25-30-35 rule of thumb for estimating average SVR in elderly females.

Figure 24:
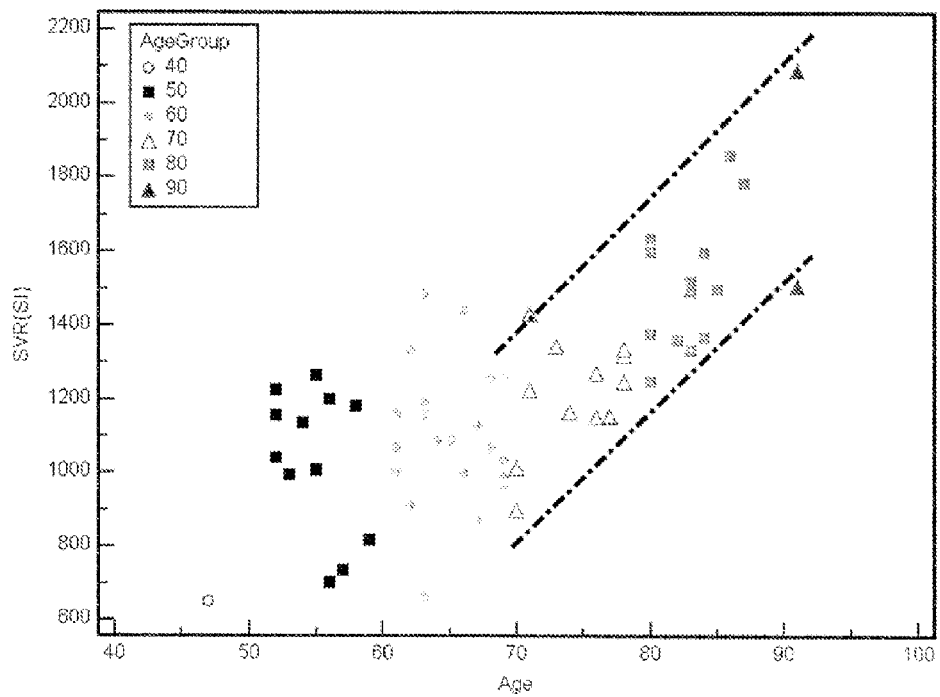
FIG. 24 shows age distribution of SVR in elderly males.

If the same analyses are performed on data obtained from elderly male patients, similar changes in CO and SVR become apparent, but the onset of the changes occurs a decade later than in elderly females and is less rapidly progressive. FIG. 24 shows a progressive increase in resting SVR in males after 70 years. The process, however is the same and has the same implications for resuscitation in anaesthesia, the emergency room and the ICU.

The inventor attributes these changes which occur with advancing age to changes in the performance of the heart as a pump. As the resting CO falls with advancing age, the SV (and SV index) falls and shows decreased variability. Whereas in younger adults, SV is continuously varied to meet power demands, in advanced age it becomes fixed.

The change in performance of the heart after about 60 years in females and 70 years in males is invariable in older patients, and represents the process elsewhere referred to as 'diastolic dysfunction'. Typically, diastolic dysfunction is characterized by reference to changes in Doppler echo parameters indicating failure of the heart as a pump. This, in turn, is characterized by falling SV and CO with advancing age leading to increased reliance on HR as a means of regulating CO. Thus, with age the heart begins to fails as a 'pump', instead becoming a passive conduit for the passage of blood around the circulation.

This has led the inventor to hypothesise that are two extremes of cardiovascular performance. The first is represented by the young athlete, who has 'flow-dependent pressure regulation' with a low fixed vascular resistance and low HR and an ability to vary SV. The second is represented by the elderly female with 'resistance-dependent pressure regulation' characterized by a fixed SV (due loss of cardiac compliance) and CO variable only by changing HR; the elderly rely on HR to increase CO and on SVR to regulate pressure.

This has important implications for understanding hypertension in the elderly: if a 90 year old female patient has a fixed SVR of 3000 dyne·sec/cm$^5$, then a 1 L/min increase in CO will cause a three-fold greater increase in blood pressure than in a fit young person with a vascular resistance of 1000 dyne·sec/cm$^5$. Small increases in metabolic demand will tend to cause marked tachycardia in the elderly because the SV cannot be varied to regulate CO.

A similar situation occurs in the regulation of CO. In the typical adult, HR and SV both continuously vary to maintain a relatively constant systemic flow. Again, there are two extremes. In the first, as occurs in athletes and the morbidly obese, the HR will be relatively low, and SV will vary widely. Thus athletes (and the obese) are SV dependent flow regulators. At the other end of the spectrum, the elderly patient with a fixed SV will be disproportionately reliant on HR, since SV is low and fixed. These individuals are therefore HR dependent flow regulators.

The corollary of an increased reliance on SVR in the face of progressive cardiac stiffness in the elderly, is an increased susceptibility to and morbidity from conditions causing pathological vasodilation. The elderly female patient with a high fixed vascular resistance will suffer a greater fall in pressure (with corresponding implications for cellular oxygen delivery) from vasodilating drugs or sepsis than will a young patient who can increase SV to increase CO and compensate for vasodilation. The elderly patient will therefore suffer more organ dysfunction and organ system failure than a young person with a similar 'septic load' simply because they are without the compensatory cardiac mechanisms present in the 'pre menopausal organism'.

The progressive inability to vary SV volume due to myocardial stiffness with advancing age is potentially attributable to the effect of androgens/estrogens on cardiac myocyte function. Cardio protective effects of estrogen in men may explain a possible association between higher levels of dehydroepiandrosterone (DHEA) and its sulfate conjugate (DHEAS) and a lower incidence of cardiovascular disease.

In view of the changing performance as the heart as a pump that occurs with advancing age, it becomes apparent that vasoactive agents employed as therapies for the elderly require re-evaluation. The practice of applying pharmacodynamic and pharmacokinetic data based on young subjects to the very elderly no longer seems appropriate. In stead, re-evaluation may require investigation of a vast database of data from a broad population to differentiate pharmacodynamics responses that are specific to age and gender. Haemodynamic mapping according to embodiments of the present invention facilitates this re-evaluation.

By applying the techniques of the present invention, the inventor has discovered that anaesthesia is often (but not always) a state of controlled shock. Using the technique of haemodynamic mapping, it can be demonstrated that patients undergoing major surgery are often in a state of 'cardiac failure' despite monitored variables being carefully controlled within normal parameters. This has profound implications for clinical anaesthesia and could explain why cognitive dysfunction (as can be identified by ischemic changes in the brain) commonly, but not always, occurs after surgery. This is demonstrated in the Examples which follow.

Accordingly, use of the present invention during surgery can be used to demonstrate, intra-operatively, that a patient is experiencing "sub-clinical shock" and non-optimal haemodynamic performance. Following on from this, use of the present invention during anaesthesia for major surgery can be used to direct therapy so as to restore optimal haemodynamic function, and to monitor and quantify the subject's response to the therapy being administered. This has the potential to eliminate masked cardiac failure to make the elderly patient who presents for surgery cognitively intact and awakes from surgery with a permanent confusional state or clinical dementia a feature of the past.

The present invention may also prove useful in determining the cerebral (and time-course) effects of anaesthetic (and other agents) under investigation as the haemodynamic mapping approach enables physicians to determine that the subject under anaesthesia is not in circulatory failure and facilitates quantification of circulatory response.

Further, the present invention provides a framework about which functional classification of shock can be implemented, based on the three kinds of shock identified. Stratification of the shock syndrome in this manner is physiologically based and provides a basis for tailored and specific individualised therapy which hitherto has not been possible. This has beneficial implications for patients undergoing surgery, resuscitation and organ dysfunction.

The present invention also provides a robust method for evaluating fluid resuscitation techniques. Current approaches to resuscitation involve unreliable end points such as urine flow in excess of 0.5 ml/kg/hr, or a MAP above 65 and CVP over 10 (Rivers). Although it presents a paradigm shift from current treatment protocols, the novel approach according to the present invention is physiologically based and has the capacity to understand better the shock syndrome and to develop resuscitation skills based on objective and evidentiary data. This has impact not only in the monitoring environment where patient data is available which can be mapped according to the invention in real time, but also in ambulatory resuscitation where newly developed skills may be applied.

The inventive method can be used to demonstrate why renal failure occurs in the patient with sepsis or SIRS or MODS. It has long been recognized that the 'inflammatory cascade' is important to the physiology of acute renal failure (ARF) in sepsis/SIRS. By mapping data according to the inventive method, one can demonstrate that the commencement of renal replacement therapy (RRT) (usually) restores vasomotor tone. It commonly improves patients haemodynamically from a point of imminent death to a position compatible with ultimate recovery. It therefore demonstrates that the principal cause of renal failure is a vasomyopathy, not an intrinsic renal disease.

This contradicts the established view that polyuria during recovery from ARF is explained by the factors of i) osmotic diuresis from accumulated urea, ii) clearance of excess fluid accumulated during ARF and iii) decreased tubular concentrating capacity. By applying the method of the present invention, it can be shown that polyuria is due to resolution of the 'vasomyopathy' as measured by a recovery of SVR and SPP. Thus, organ system failure in SIRS is a vascular disease rather than an organ based disease.

Further, the inventive techniques can be used to demonstrate that in established sepsis/SIRS/MODS, when there is cardiac involvement in the multiple organ dysfunction, the cardiac lesion is diastolic dysfunction.

The present invention can also be used to demonstrate the phenomenon of acute circulatory failure from bacteraemia. This can occur with apparently stable blood pressure and pulse rate. However, mapping patient data in a visual representation according to the present invention suggests that the acute vasomyopathy induced by bacteraemia may be a more powerful influence on the circulation than relative hypovolaemia. If a transient bacteraemia increases cardiac output under anaesthesia, it may be possible to identify a non-infective component of the bacterial cell wall as a therapeutic agent for use in anaesthesia.

Furthermore, the techniques of the present invention are sufficiently sensitive to vasoactive agents that it can facilitate decoding of the haemodynamic profiles of vasoactive and cardio-active drugs. It may be sensitive enough to differentiate inter-individual variation in drug responsiveness, and not only detect responders and non-responders to drugs, but selectively identify patients with genetic 'polymorphisms' which alter vascular responsiveness.

In embodiments which adjust for compensatory changes in HR, the present invention may also be used to differentiate populations of individuals whose responsiveness to a particular drug differs from other populations, and evaluate the nature and magnitude of that difference.

This model also leads to very different approaches to diagnosis and treatment. For any treatment, the effect on the circulation can easily be identified. When applied to septic patients, the present invention will permit accurate risk stratification and better targeted selection and application of treatments. The invention can also be used to explain the physiological development of multiple organ dysfunction in critically ill patients and may challenge long established beliefs regarding the actions of drugs and the cause of polyuria in resolving renal failure.

It is believed that until now, there has been no method or system for establishing, in the individual patient, the "autoregulatory range" of blood pressures in which constant cardiac output is maintained. However, mapping a continuous data stream of variables from the subject according to the present invention enables the identification of a 'lower inflection point' or a "set point" of the autoregulation zone, which divides the normal autoregulation from the 'drop off zone'.

Since this point is identifiable there is a point unique to every subject toward which therapy should be directed.

The potential uses of the visual representations obtainable using the haemodynamic mapping technique of the present invention and the possible benefits in patient care, reduced morbidity and mortality as well as reduced financial and social costs are many. In addition to eliminating risks associated with cardiac failure during an aesthesia, the invention may also prove useful in detection and identification of risk factors for syndromes such as deep vein thrombosis and pulmonary embolism as these may be identified as a complication of a sub-clinical low-flow state which is entirely preventable with appropriately targeted therapy.

Perhaps most importantly, the techniques of the present invention make it possible to detect trends in heart failure well before there are clinical signs of the shock syndrome. This has enormous implications for the conduct of anaesthesia, and the finding of cognitive dysfunction and other organ dysfunction after prolonged surgery.

Furthermore, as has been discussed in the foregoing the techniques of the present invention enable physicians to objectively and quantitatively assess bulk data representative of various patient groups (e.g. females 60 years and older, males 70 years and older) to understand in real terms how aging influences haemodynamic performance and pharmacodynamics. This enables physicians to monitor the elderly and elderly female patients in particular, to monitor closely the extreme dependence of blood pressure on vascular resistance, and target pharmacotherapy according to the actual or expected haemodynamic performance of those subgroups. It is expected that targeted therapy utilising haemodynamic mapping techniques will markedly reduce the morbidity of anaesthesia which is presently unacceptably high in elderly females.

Further, it is widely appreciated in anaesthesia that some patients respond to pressure therapy and others respond better to different vasodilators, vasoconstrictors and the like. Although these vagaries have been accepted in the past without explanation, haemodynamic mapping according to embodiments of the present invention provide a quantitative vehicle for understanding the physiological response behind these differences.

It also has enormous implications for the investigation of drug effects (pharmacodynamics) since a drug effect under anaesthesia cannot be attributed to a drug unless it is first known that the patient was not in a state of 'physiological shock' during the study period.

It is to be understood that various modifications, additions and/or alterations may be made to the parts previously described without departing from the ambit of the present invention as defined in the claims appended hereto.

The following examples demonstrate application of the inventive method in the clinical setting.

Example 1

Figure 9A:
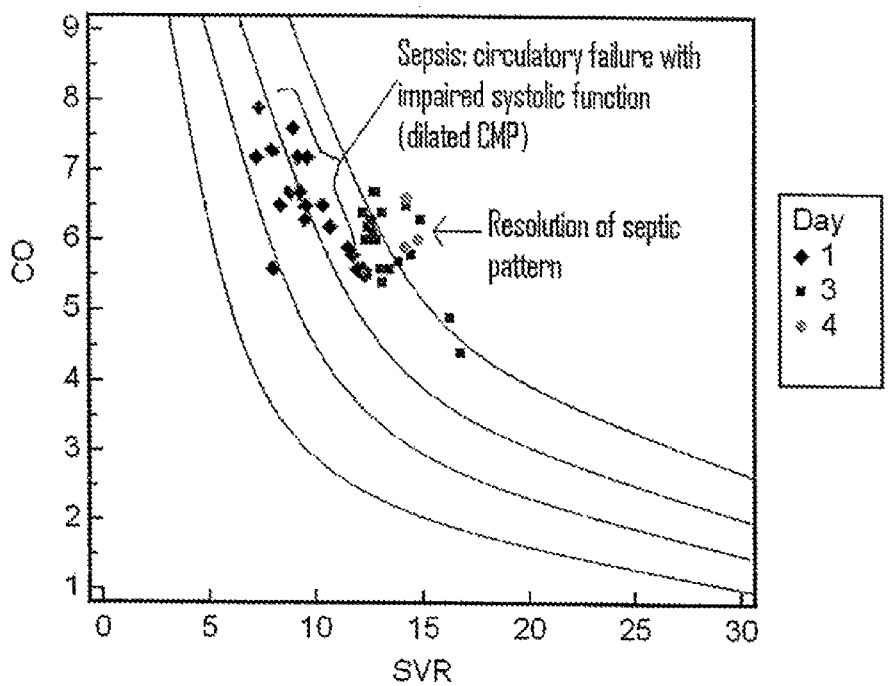
FIGS. 9a and 9b show patient data obtained using an embodiment of the present invention and discussed in Example 1.
Figure 9B:
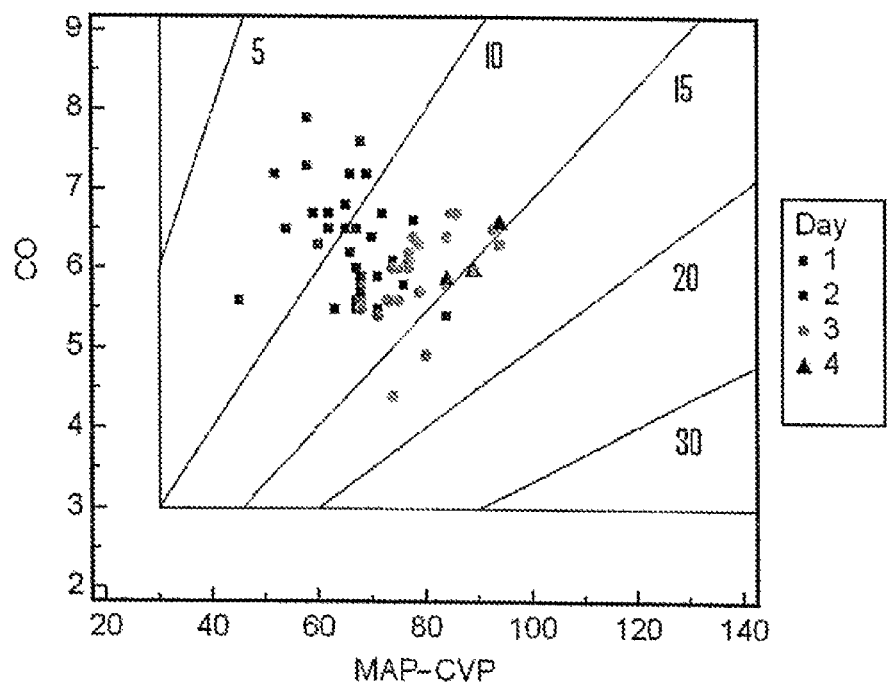

80 year old male with dilated cardiomyopathy admitted with *Pseudomonas*, urinary tract infection (UTI) and worsening renal function. This patient illustrates sepsis with systolic dysfunction. The haemodynamic mapping in FIG. 9a shows that on admission the patient is in circulatory failure (i.e. failure of the vascular pump) as is evident by the trend of day 1 data along the third isobar (compare with pattern represented in FIG. 8a). Because of a dilated cardiomyopathy, systolic dysfunction prevents the subject from maintaining the systemic perfusion pressure at his physiological autoregulation zone. As he responds to treatment, the mapping shows that his circulation returns to the zone of normal autoregulation (see day 3 and day 4 data) coinciding with normalization of renal function and cessation of inotropic support. The autoregulation zone when represented in flow-pressure format (iso-resistance nomogram in FIG. 9b) also shows progressive recovery over 3 days.

As discussed in the body of the specification, this example shows a pattern of Type 1 shock manifested by a fall in SVR, an increase in CO, and a SPP at the baroreceptor 'set point'. Because of a dilated cardiomyopathy, this septic patient is not able to fully compensate for loss of vasomotor tone.

Example 2

79 year old female undergoing right hemicolectomy and transabdominal oesophagectomy. Pre-induction CO at rest is 5.9 (the resting pre-induction CO is the physiologic autoregulation zone and is valuable in reading the 'haemodynamic map'). The autoregulation zone in flow-pressure format (iso-resistance nomogram in FIG. 10a) shows a clear 'heart failure' pattern during anaesthesia in the operating theatre (OT data).

Figure 10A:
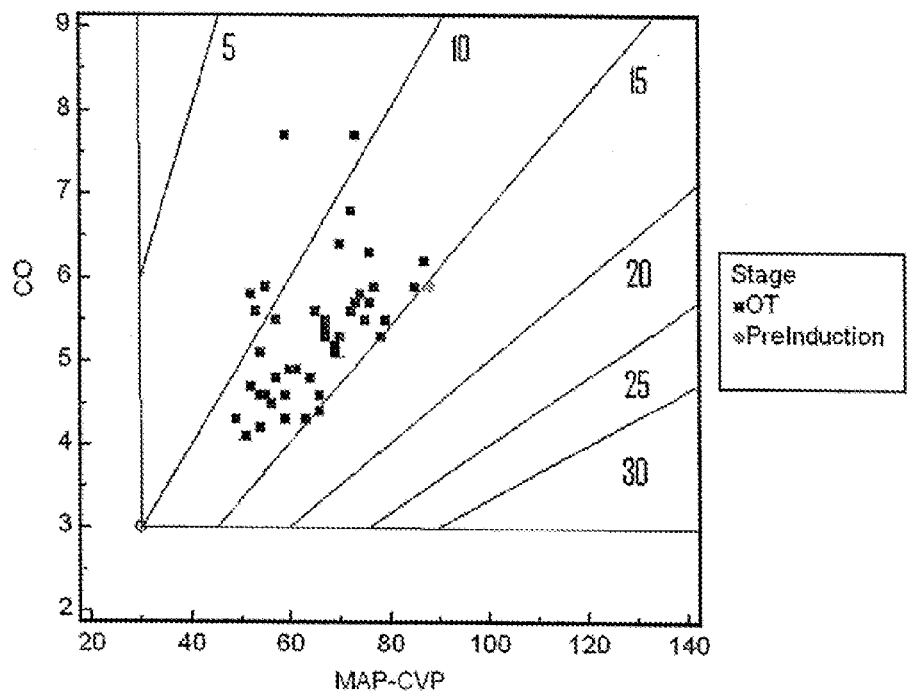
FIGS. 10a and 10b show patient data obtained using an embodiment of the present invention and discussed in Example 2.
Figure 10B:
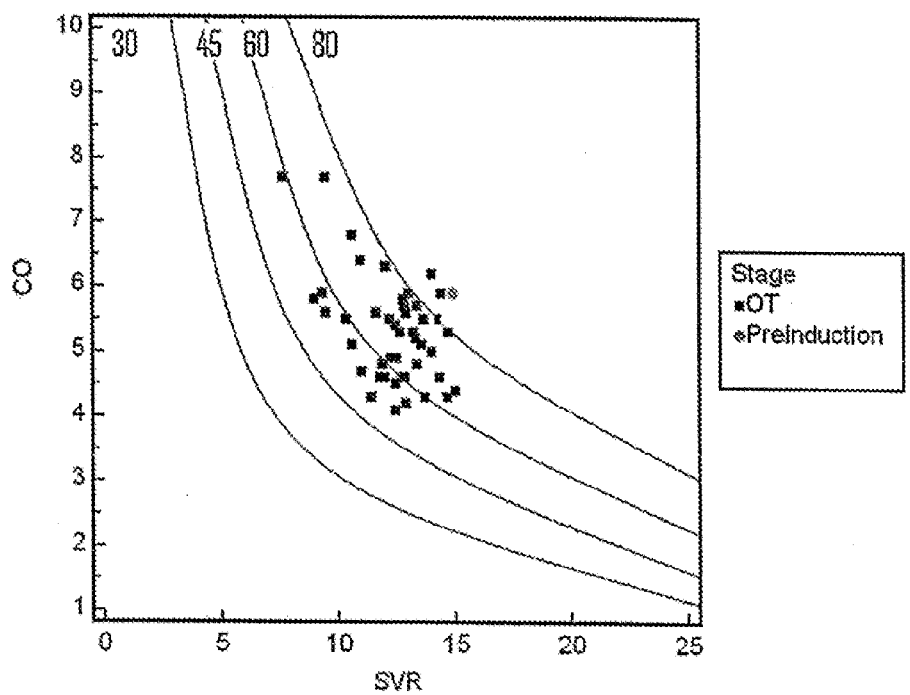

If this patient were in the normal autoregulation range, the data values in FIG. 10a would trend horizontally and to the right of the pre-induction value as shown by the solid line in FIGS. 6a-6d. However the data trends downward in FIG. 10a along an iso-resistance line corresponding to the representation of Type 3 shock as represented in the shock pattern of FIG. 6c. Knowing this value is also useful in interpreting the 'isobar nomogram' illustrated in FIG. 10b. Here, we see the patient data trending downward from the autoregulation zone again showing a pattern consistent with Type 3 shock as represented in FIG. 8c.

Example 3

Figure 11A:
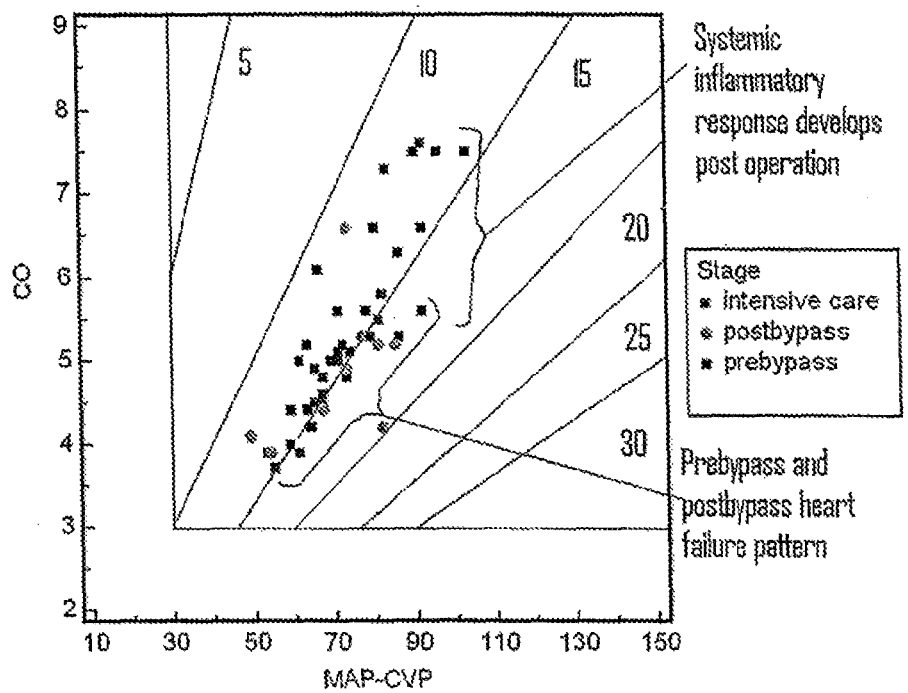
FIGS. 11a and 11b show patient data obtained using an embodiment of the present invention and discussed in Example 3.

Healthy 62 yr male with normal left ventricular function undergoing Coronary Bypass Surgery. The autoregulation zone in FIG. 11a shows a 'heart failure' pattern pre-bypass and post-bypass (compare with Type 3 shock as represented in FIG. 6c), and an inflammatory pattern developing post-operation in ICU (compare with Type 1 shock as represented in FIG. 6a).

On arrival in intensive care, the patient is developing a systemic inflammatory response, so the pattern changes to a Type 1 (sepsis like) pattern. From the mapping in FIG. 10b, the autoregulation zone appears to be around 80 mmHg, at the inflection between the heart failure pattern and the inflammatory pattern. Postoperatively, this patient developed the usual inflammatory response pattern.

Figure 11B:
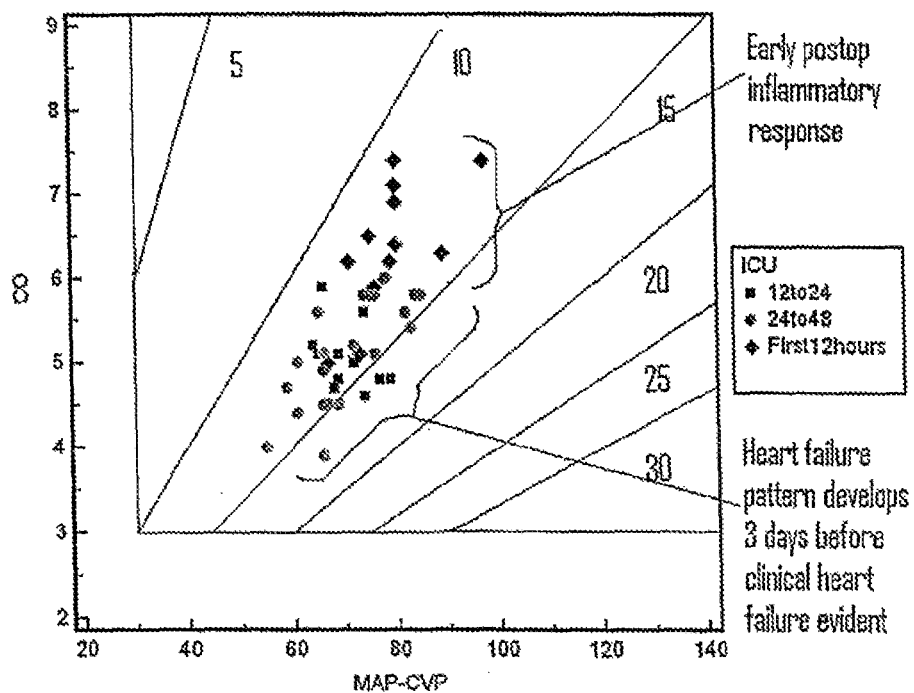

Two days after surgery, when he was hypotensive and oliguruc, the haemodynamic data was mapped again (FIG. 11b) and it unexpectedly showed a 'heart failure' pattern, even though the patient had no clinical signs of heart failure. Since he appeared clinically well, the subject was sent to the surgical ward. Three days later, he had clinically evident heart failure with bipedal edema and low serum sodium. Haemodynamic mapping was able to identify the presence of a heart failure pattern 3 days before it was clinically obvious.

Example 4

Figure 12A:
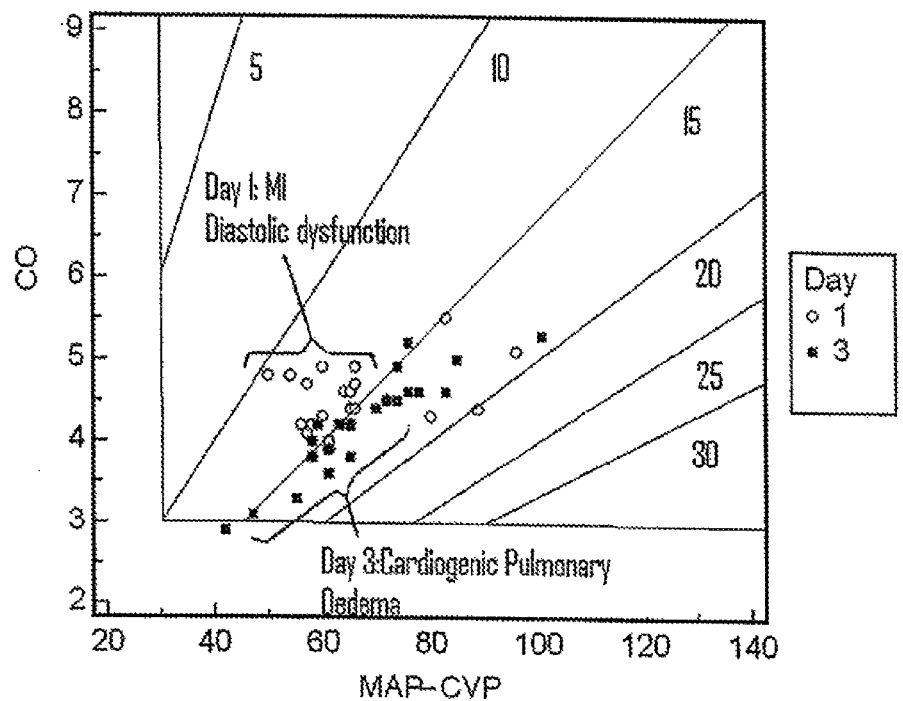
FIGS. 12a to 12d show patient data obtained using an embodiment of the present invention and discussed in Example 4.

63 year old male with aortic stenosis and coronary disease who underwent AV replacement and coronary artery grafting. Postoperatively (day 1), he had a large anterior infarct. The flow-pressure curve (iso-resistance nomogram in FIG. 12a) shows a Type 2 pattern, i.e. circulatory failure with diastolic dysfunction (compare with the pattern of FIG. 6b). The patient underwent angioplasty and improved. On Day 3, he deteriorated and clinically had cardiogenic pulmonary edema (Type 3—compare with the pattern in FIG. 6c) which again is clear from the mapping in FIG. 12a.

Figure 12B:
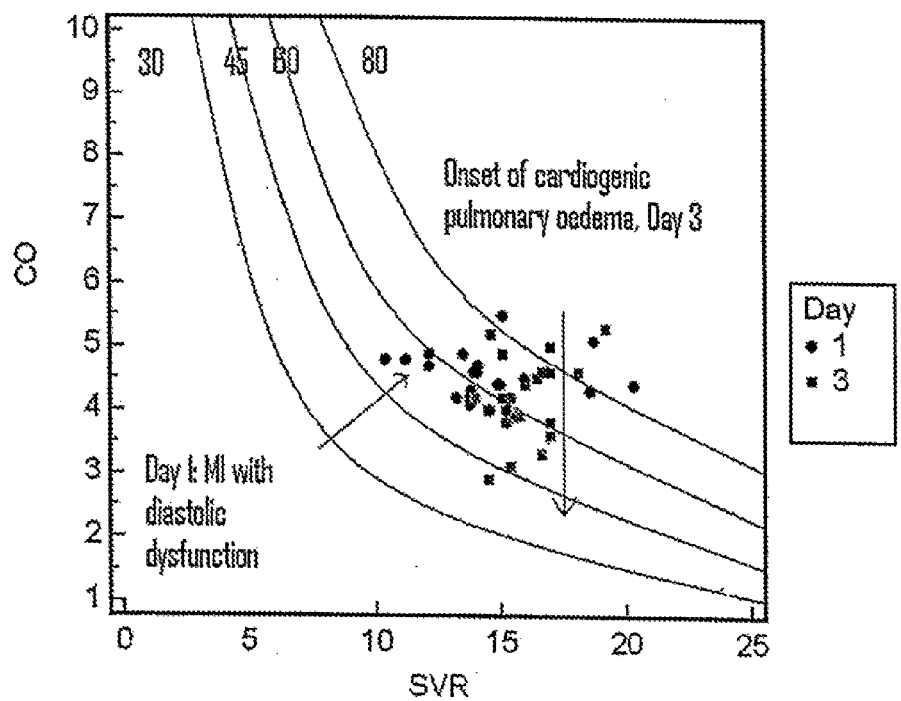

Similarly, the isobar nomogram in FIG. 12b shows a trend toward Type 2 shock in day 1 (compare with the shock pattern in FIG. 8b) and Type 3 shock in day 3 (compare with the shock pattern in FIG. 8c).

Figure 12C:
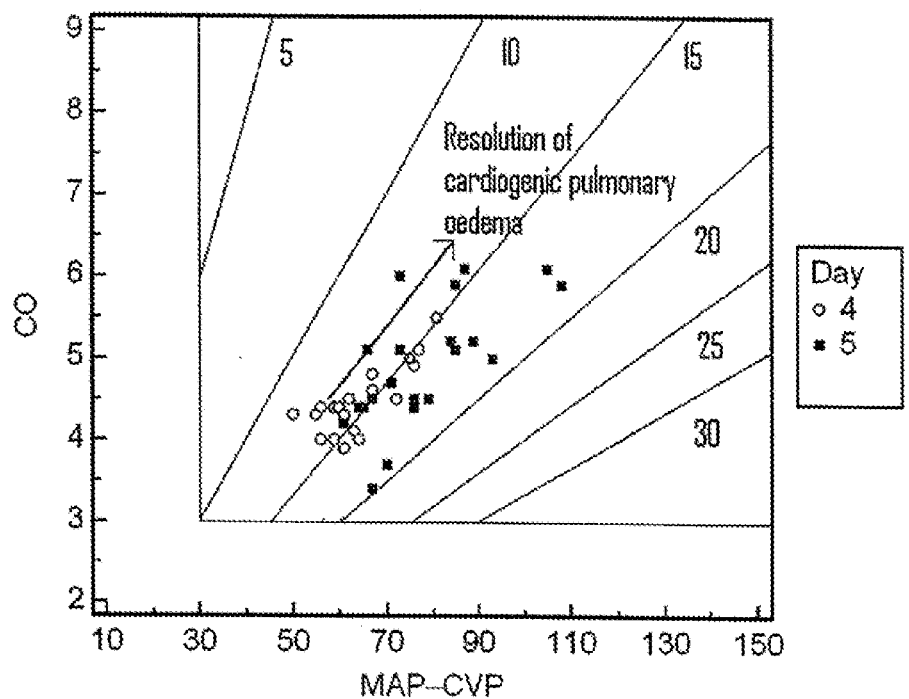
Figure 12D:
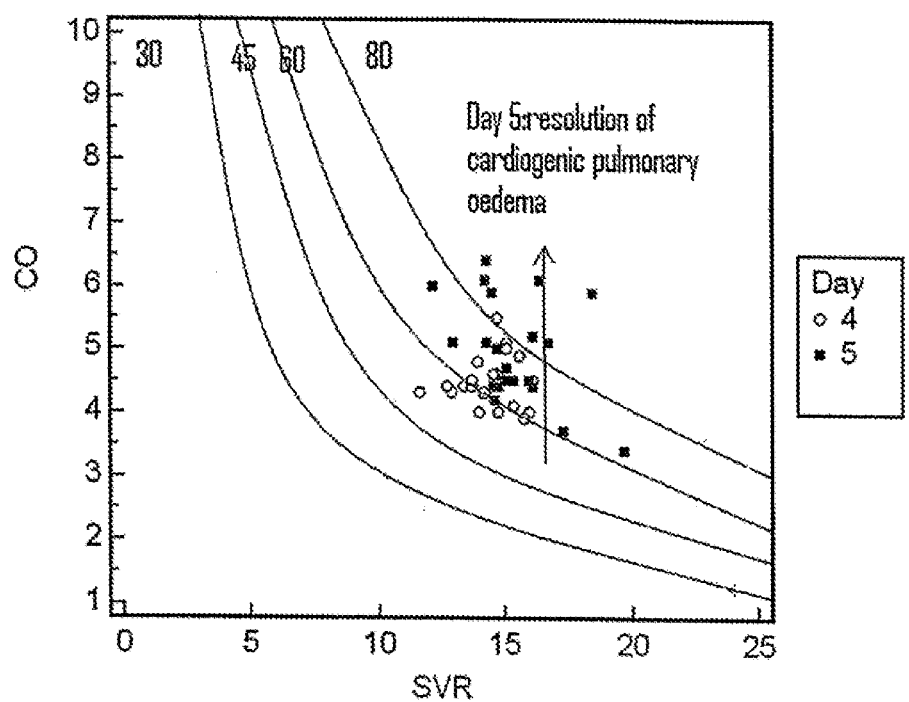

The patient was reventilated, and treated for pulmonary edema with lasix and dobutamine. With a large diuresis, he improved from day 4 to day 5, and was well enough to be extubated. FIGS. 12c and 12d show in flow-pressure and resistance-flow formats respectively and recovery from Type 3 shock patterns to a pattern more representative of an autoregulation set-point trending toward a horizontal line in the isobar nomogram (FIG. 12c) for day 5 data.

Example 5

Figure 13A:
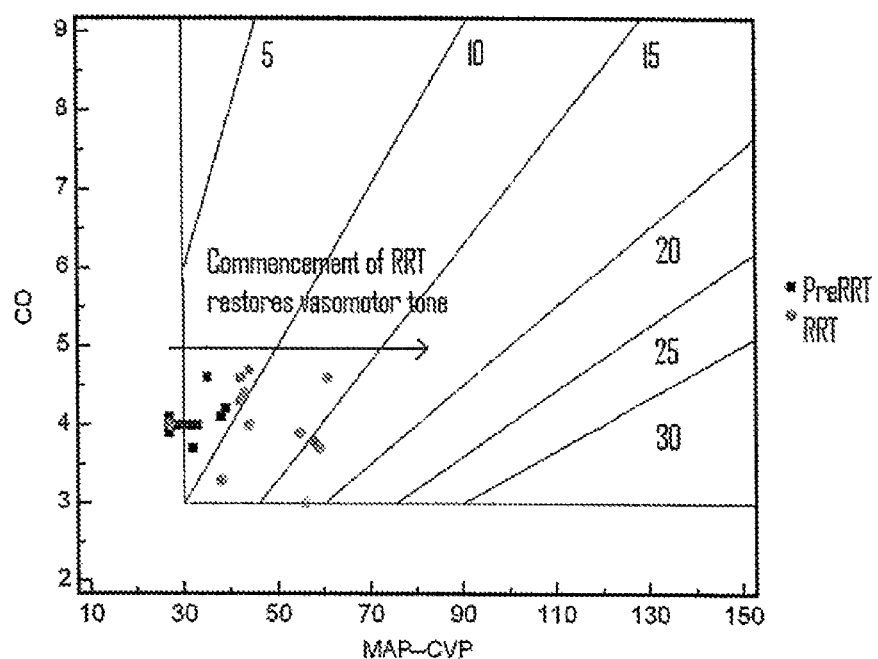
FIGS. 13a to 13d show patient data obtained using an embodiment of the present invention and discussed in Example 5.
Figure 13B:
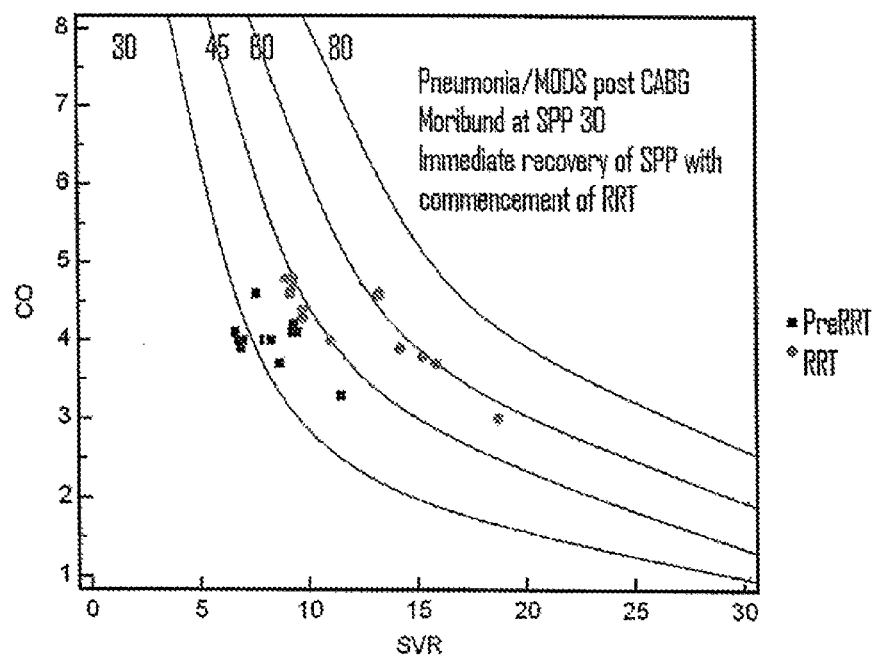

81 year old male with bronchiectasis, underwent coronary bypass surgery, uneventfully. On day 4, he develops clinical lobar pneumonia, and becomes oliguric. His systemic perfusion pressure drops to 30-40 mmHg, so he is reventilated and dialysed. The visual mapping in FIGS. 13a (iso-resistance nomogram) and 13b (isobar nomogram) for PreRRT and RRT data show sudden recovery in vasomotor tone with commencement of RRT. This restores the perfusion pressure compatible with ultimate recovery.

Figure 13C:
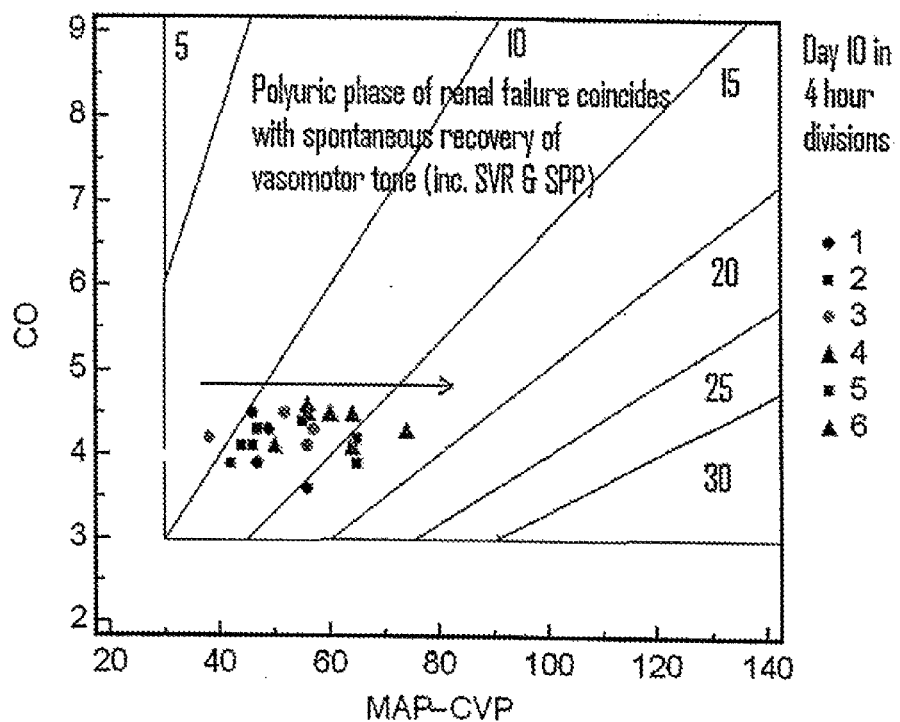
Figure 13D:
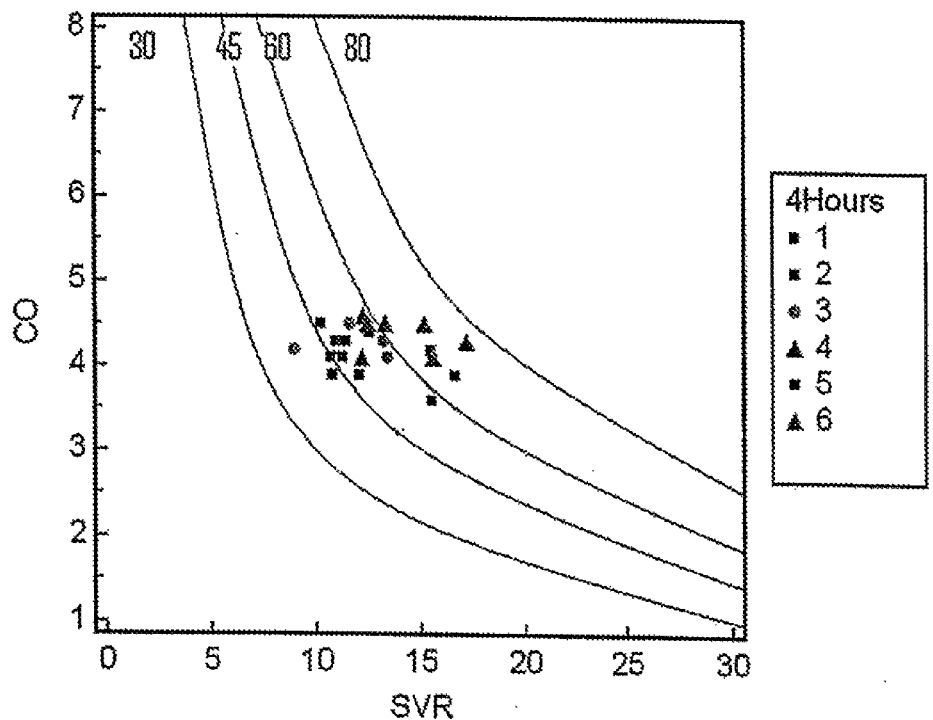

On day 10 after admission, without diuretics, the patient develops a spontaneous diuresis. Conventional teaching in medicine says this is due to 1) urea induced osmotic diuresis, 2) accumulated water, and 3) decreased tubular concentrating capacity. The haemodynamic mapping of this patient on day 10 suggests that the kidneys are normal, and the fundamental problem is vasomotor tone, which suddenly recovers. Presumably, then, the oncotic pressure of circulating albumin is able to 'suck out' the increased interstitial fluid. See FIGS. 13c and 13d.

Example 6

Figure 14A:
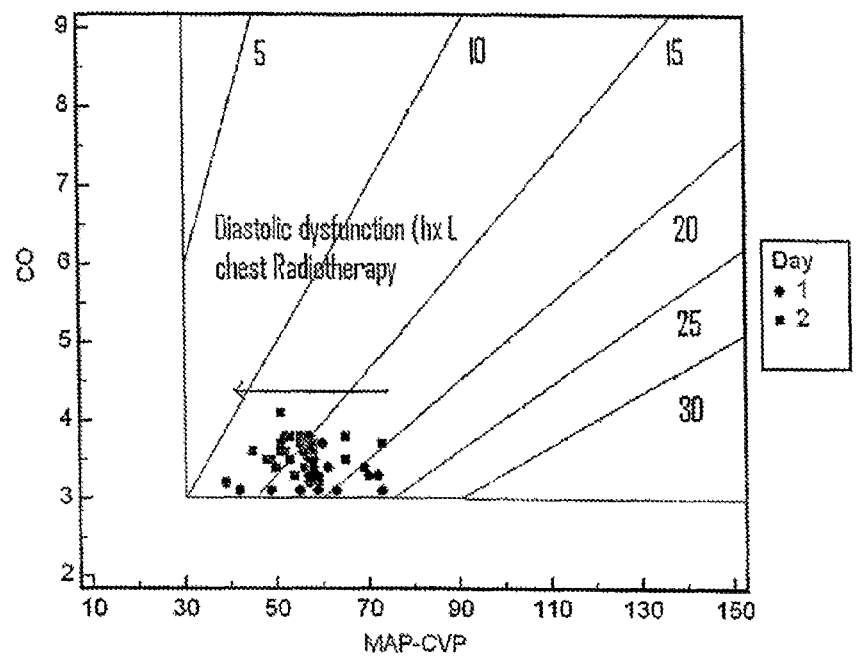
FIGS. 14a to 14c show patient data obtained using an embodiment of the present invention and discussed in Example 6.
Figure 14B:
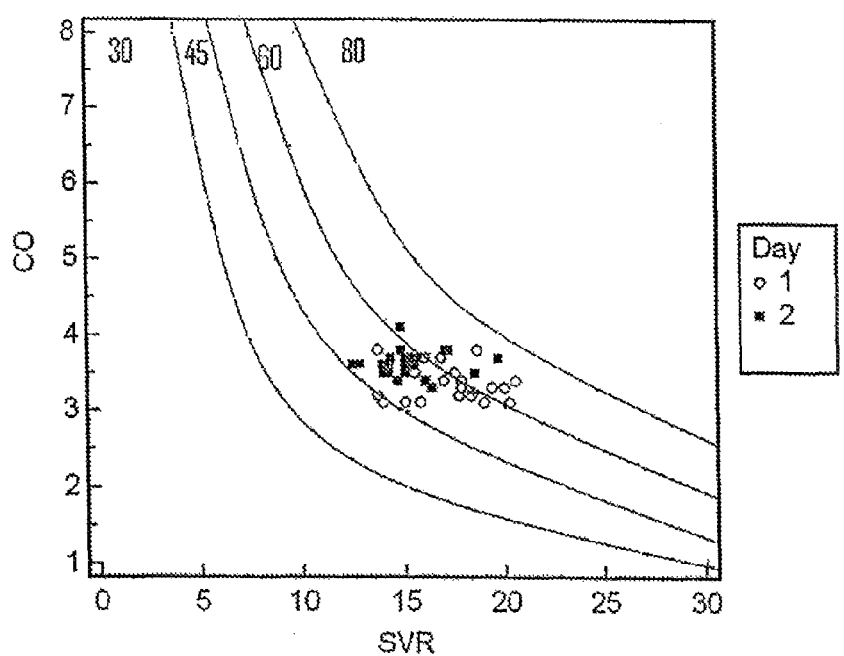
Figure 14C:
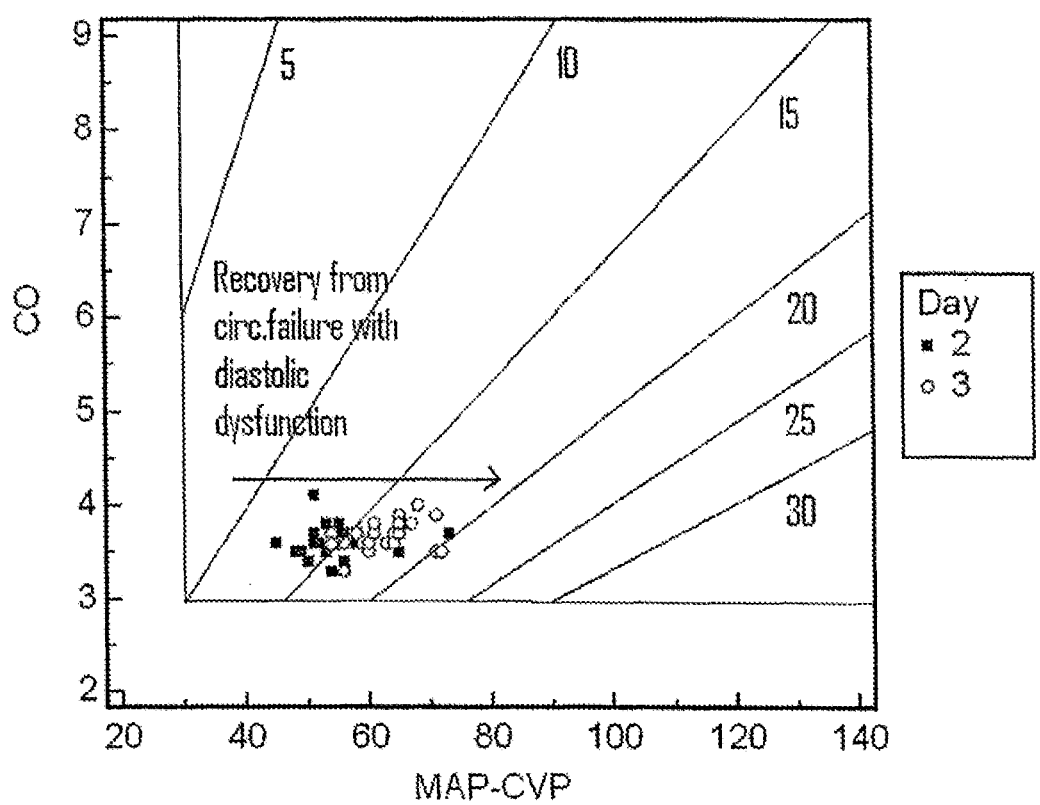

65 yr old female patient with coronary disease. Past history of left mastectomy and radiotherapy. Irradiation over the heart causes myocardial disease. This patient is unable to mount a normal cardiac response to the postoperative 'circulatory failure' and shows a Type 2 pattern (i.e. diastolic dysfunction) as shown in FIGS. 14a (iso-resistance nomogram) and 14b (isobar nomogram) (compare with the patterns represented in FIG. 6b). On the third day after surgery, this recovers. See FIG. 14c.

Example 7

Figure 15A:
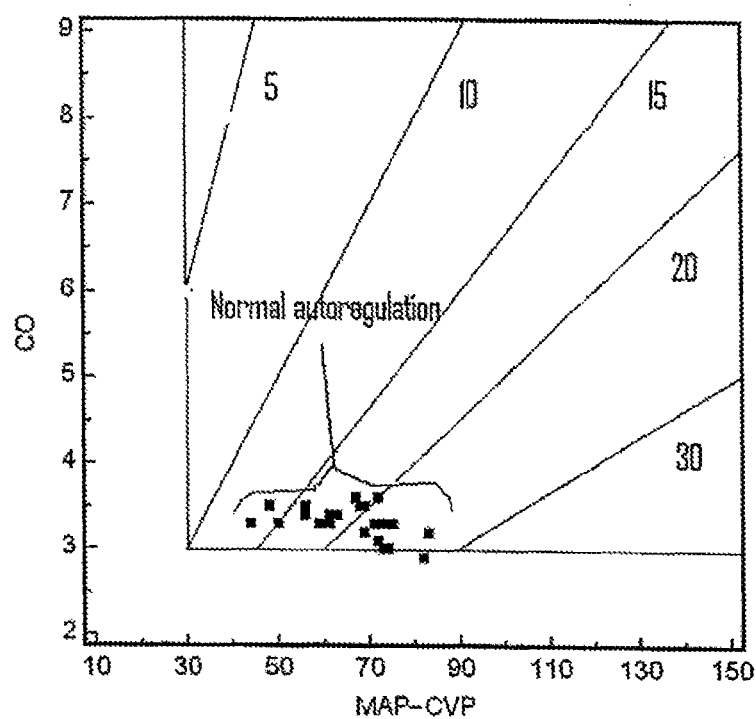
FIGS. 15a to 15c show patient data obtained using an embodiment of the present invention and discussed in Example 7.
Figure 15B:
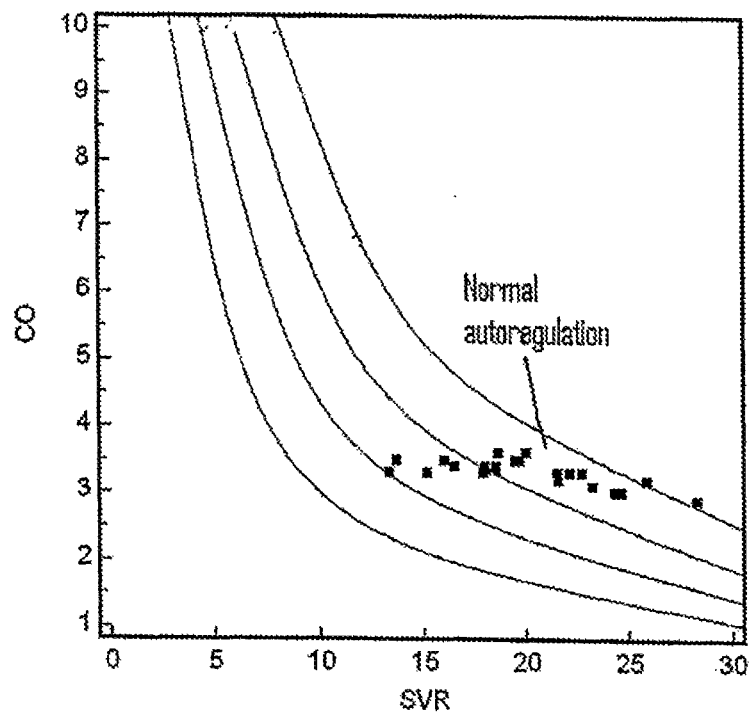
Figure 15C:
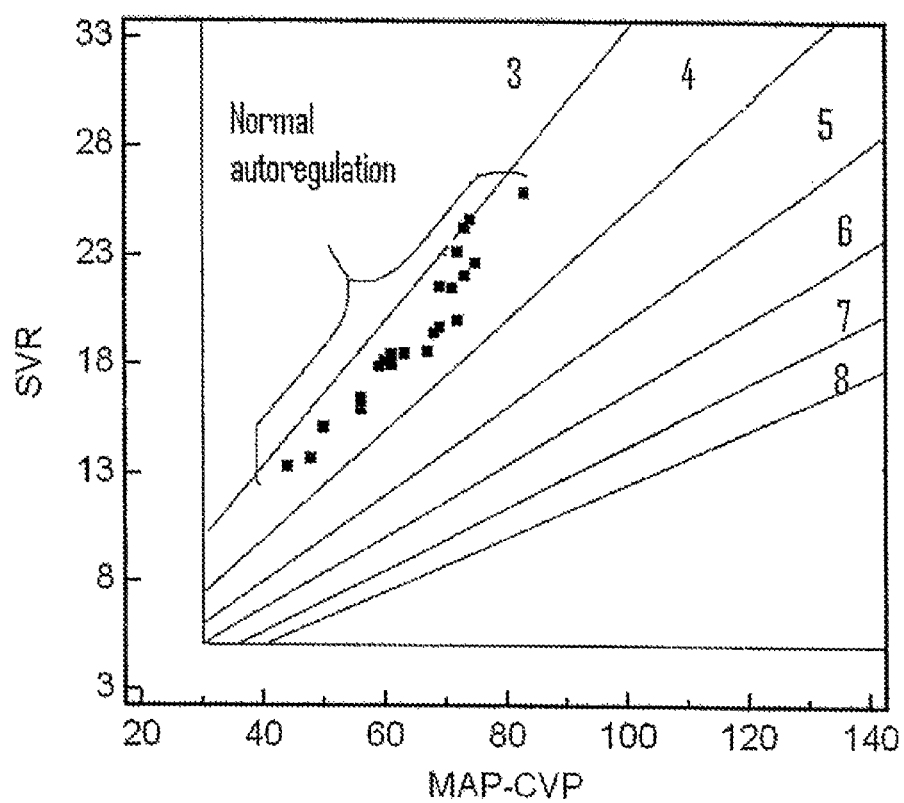

This example shows normal autoregulation. It is not usually possible to study normal autoregulation in the hospital population. This is a 94 yr old woman who became obtunded 7 days after total hip replacement due to hyponatraemia. She was cardiovascularly well, so data was collected to examine the normal process of autoregulation. These are represented in an iso-resistance nomogram in FIG. 15a, an isobar nomogram in FIG. 15b and an isoflow nomogram in 15c.

Case Study 1—79 yr Male, Ischaemic Heart Disease, Recent Cerebrovascular Accident (CVA), Undergoing 'Off Pump Coronary Bypass Grafting'

Figure 25:
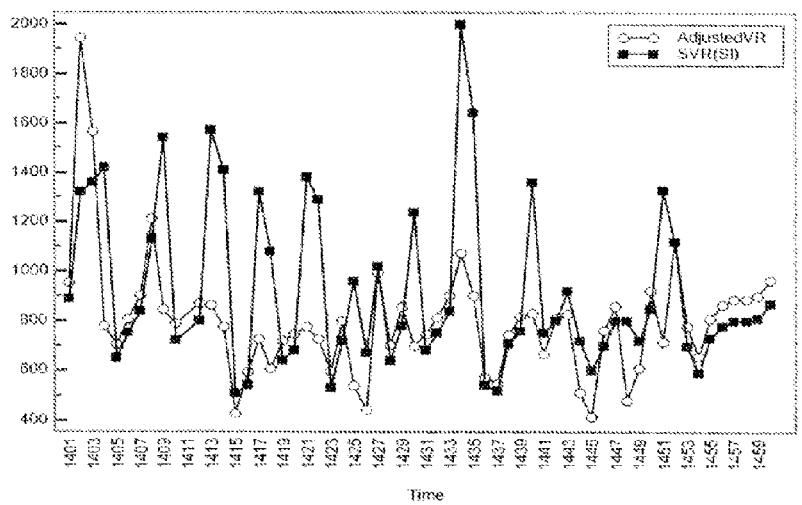
FIG. 25 shows time variability of SVR and aSVR with HR for the subject in Case Study 1.

While the heart was extrinsically compressed during grafting, the heart developed a recurring brady-arrhythmia. The HR changed to approximately 40 beats/min and then flipped back to a faster intrinsic rate at approximately 80 beat/min. When the SVR and aSVR were simultaneously graphed during this period, there were considerable differences between the respective values (FIG. 25). The aSVR changes very little with HR, compared with unadjusted SVR.

Case Study 2—67 yr Male, Coronary Artery Disease, Underwent (on Pump) Coronary Bypass Grafting.

Figure 26A:
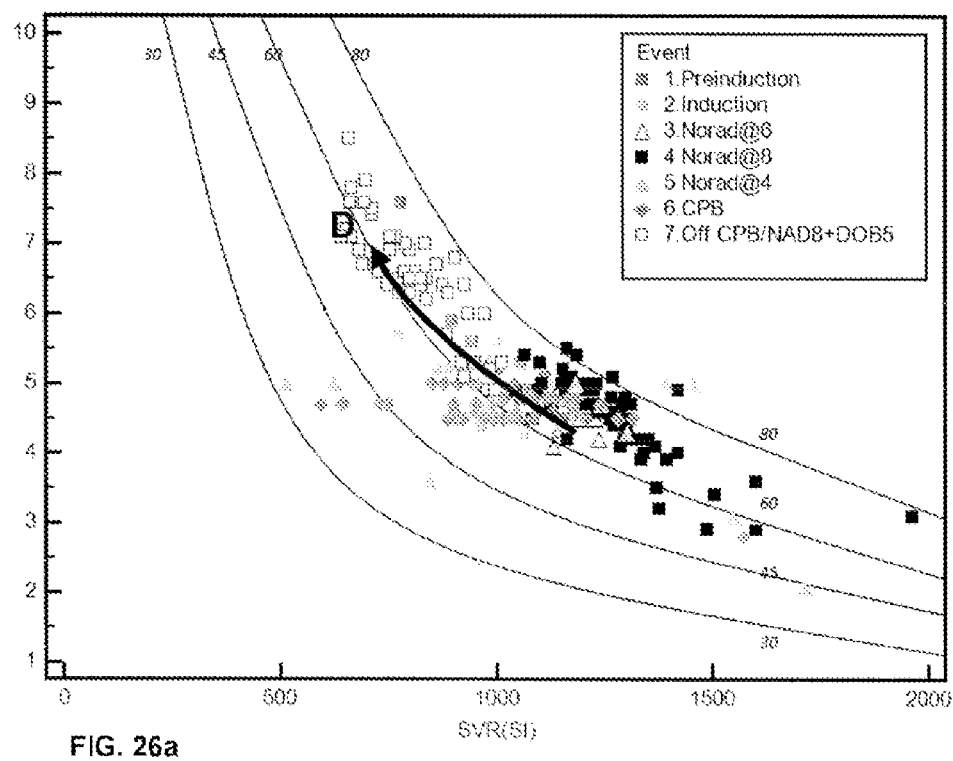
FIG. 26a maps CO against SVR.

Prior to bypass, he was on 8 ml/hr noradrenaline. On weaning from bypass, this was supplemented with 5 ml/hr dobutamine. The graph of CO against SVR (FIG. 26a) shows that, compared to the prebypass period, he was vasodilated with the addition of dobutamine, but with a significant improvement in cardiac output. This is consistent with the known effects of dobutamine which, in addition to noradrenaline when coming off bypass, sees a decrease in SVR and an increase in CO. Pressure is unchanged (See trend line D).

Figure 26B:
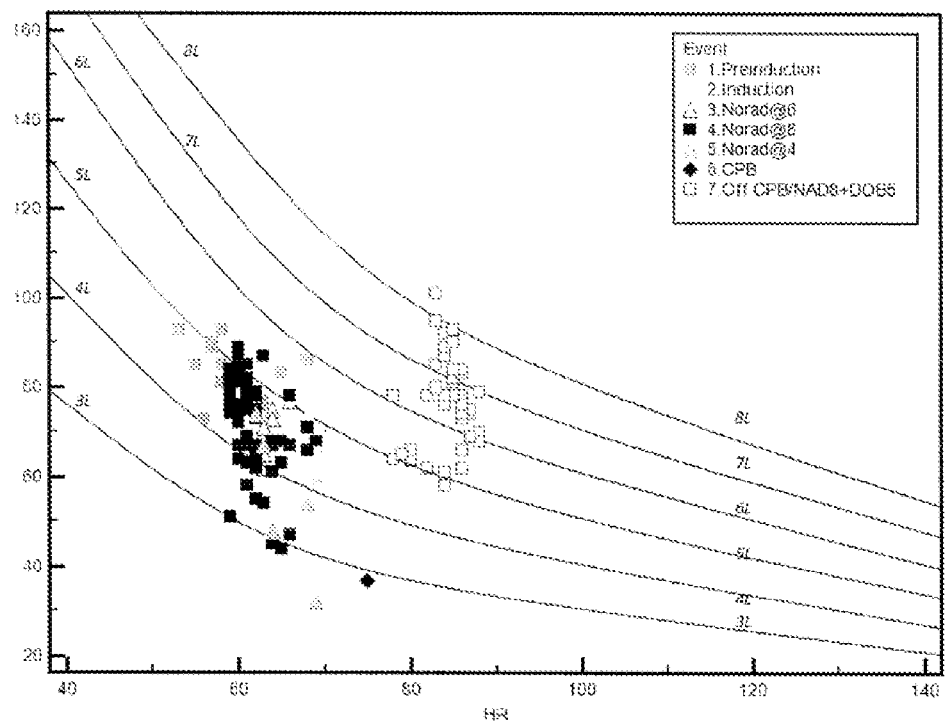
FIG. 26b maps SV against HR.

However, when this data is subjected to further analysis flaws become evident. Plotting SV and HR (FIG. 26b) for the periods before and after cardiopulmonary bypass reveal that the addition of dobutamine made no difference to SV although HR increased by nearly 50%, accounting for the improvement in CO (since CO=HR×SV).

Figure 26C:
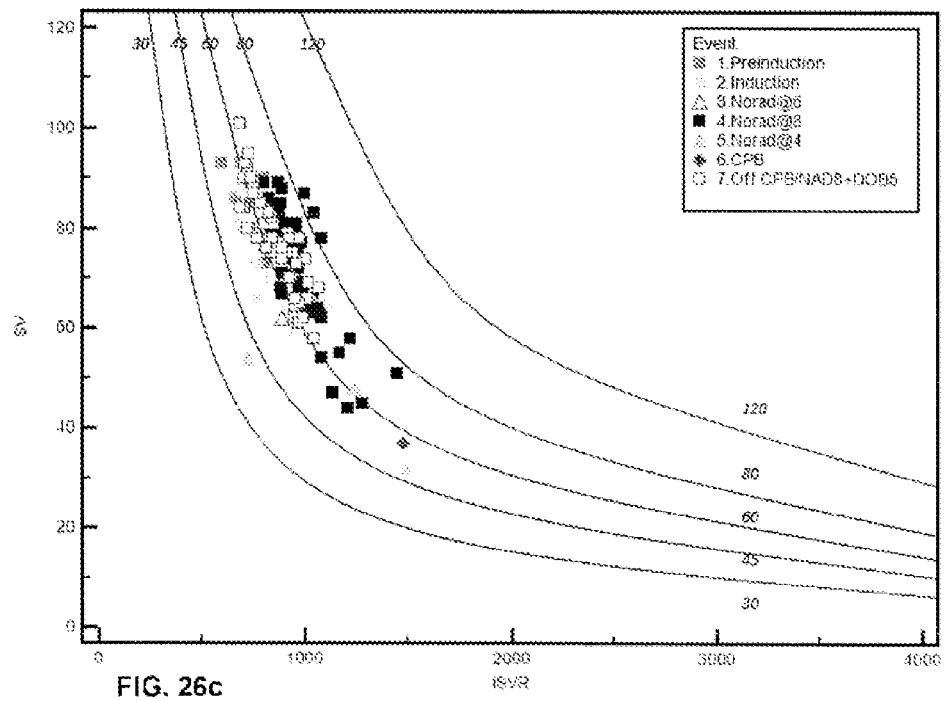
FIG. 26c maps SV against aSVR; all for the subject in Case Study 2.

Mapping the relationship between SPP, SV and aSVR (FIG. 26c) reveals no change in aSVR or SV when dobutamine is added, there is merely an increase in HR. This analysis leads to a conclusion that dobutamine is not an inotrope and not a vasodilator. The effect is merely artefactual, because SVR per se is not corrected for the increase in HR resulting from the addition of dobutamine (Note: aSVR is plotted in mmHg/mL not mm Hg/L).

Case Study 3—80 yr Female, Laparoscopic Fundoplication, Developed Atrial Fibrillation Post-Operatively in ICU.

Figure 27A:
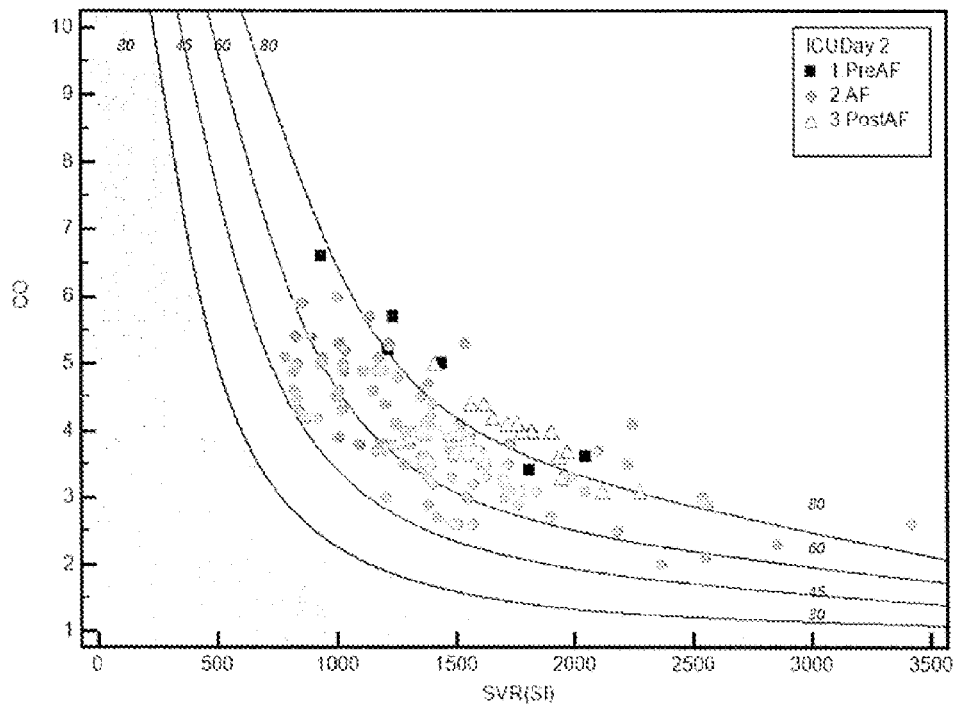
FIG. 27a is an isobar nomogram.
Figure 27B:
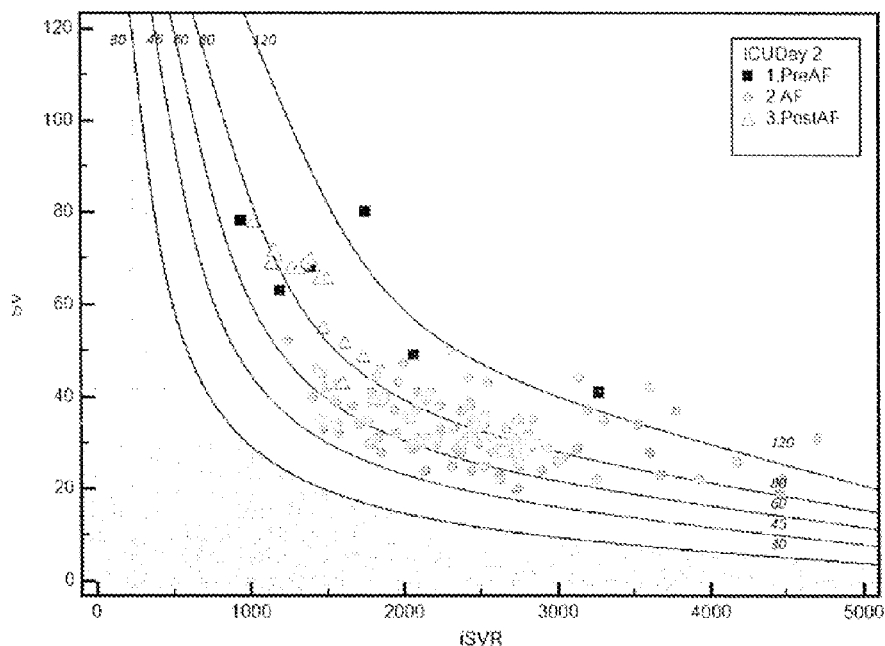
FIG. 27b is an isobar nomogram corrected for HR and mapping SV and aSVR for the subject in Case Study 3.

This was successfully treated with amiodarone, and she reverted to sinus rhythm. Hitherto, it was believed clinically that atrial fibrillation is associated with haemodynamic compromise and peripheral vasoconstriction (increase in resistance). However, if SVR is calculated continuously in the presence of acute AF, it often appears that vascular resistance decreases. This is illustrated in the isobar nomogram of FIG. 27a. However, a mapping of SV and aSVR (FIG. 27b), confirms the existence of vasoconstriction. Because SVR is equal to aSVR/HR, when a patient develops a tachycardia, the SVR will decrease, even when the actual vascular resistance is either unchanged or actually increases.

Case Study 4—57 yr Overweight Male Patient, Bilateral Total Knee Replacement.

Figure 28A:
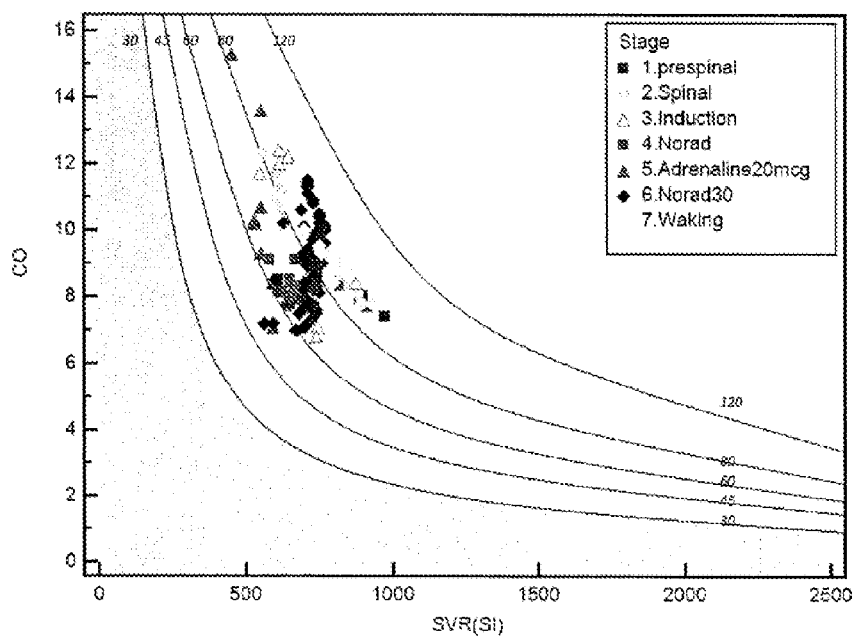
FIG. 28a is an isobar nomogram.
Figure 28B:
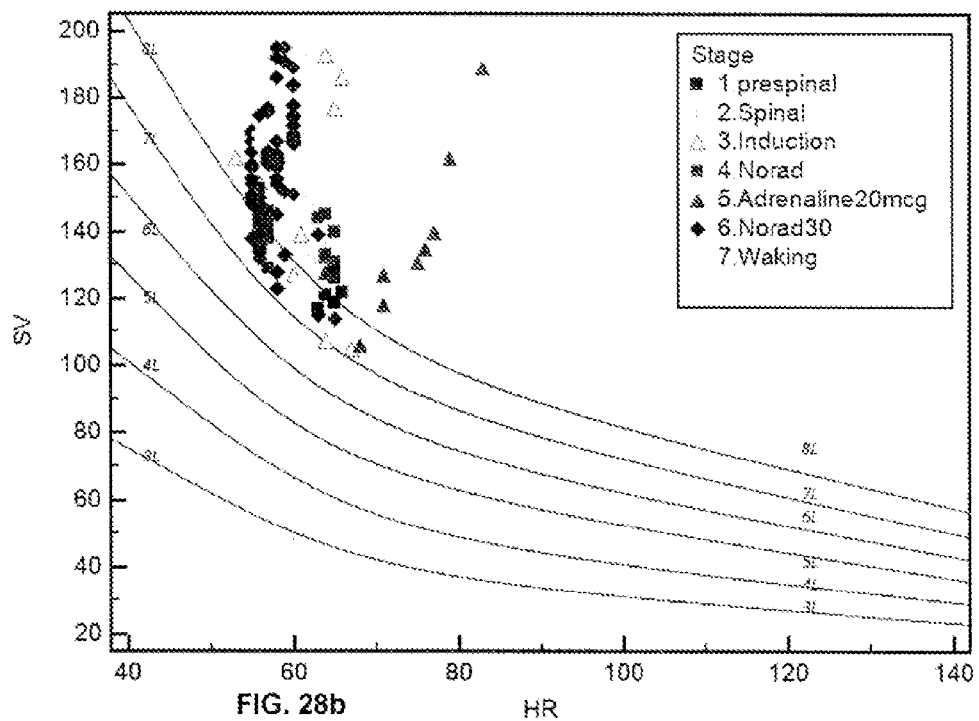
FIG. 28b maps SV and HR.
Figure 28C:
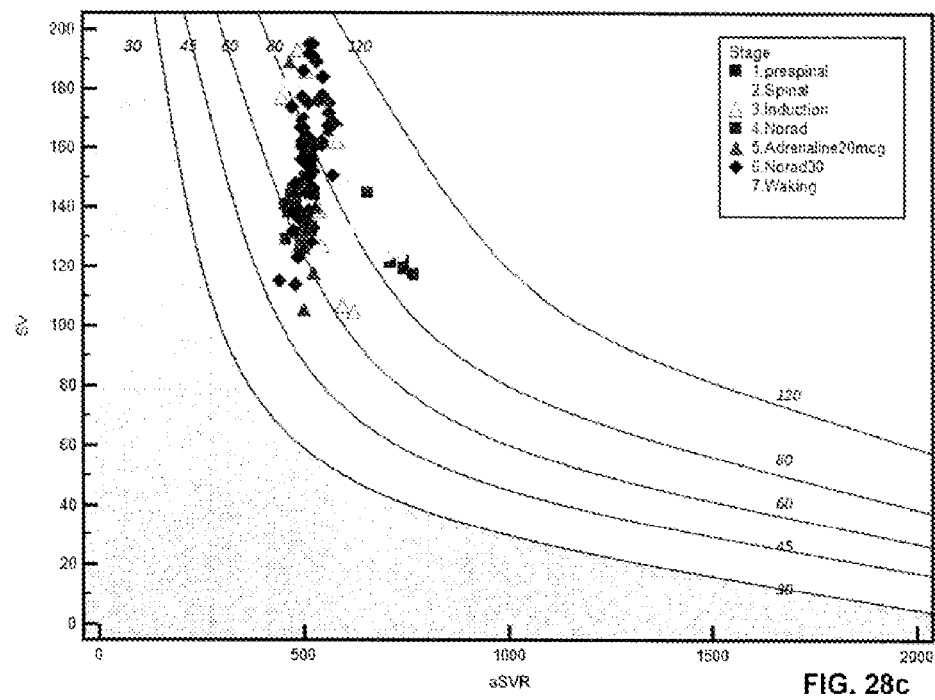
FIG. 28c is an isobar nomogram corrected for HR and mapping SV and aSVR for the subject in Case Study 4.

The patient became hypotensive during anaesthesia, and was given 20 mcg adrenaline, resulting in an increase in HR, and a calculated fall in SVR (FIG. 28a). Later, he was started on a noradrenaline infusion at up to 30 ml/hr (20 mcg/min). When SV is mapped against HR (FIG. 28b), both adrenaline and noradrenaline are seen to increase SV to a similar extent, but adrenaline causes a rise in HR, and noradrenaline is associate with a fall in HR. However, in a mapping of aSVR and SV (FIG. 28c), neither adrenaline or noradrenaline has an effect on vascular resistance. Once HR is corrected for, it is seen that the effect of these drugs on vascular resistance in this patient is merely artefactual.

Case Study 5. Sepsis in a Young Male Patient.

A healthy obese 57 yr old male pharmacist underwent laparoscopic gastric banding. 13 months later, following upper GI symptoms, a gastroscopy revealed band erosion into the gastric lumen. Two days later, the band was removed laparoscopically, and initial postoperative course was uneventful. 24 hours following surgery, he experienced sudden onset of severe abdominal pain, with features of peritonism. At laparoscopy, there was a hole in the stomach at the site of the band, with pus oozing into the peritoneal cavity. The wound was closed, but the patient later developed a subphrenic abscess. Haemodynamic mapping of data obtained during manipulation of the infected perforation showed a profound drop in vascular resistance with a compensatory rise in CO although SPP remained essentially normal.

Figure 29:
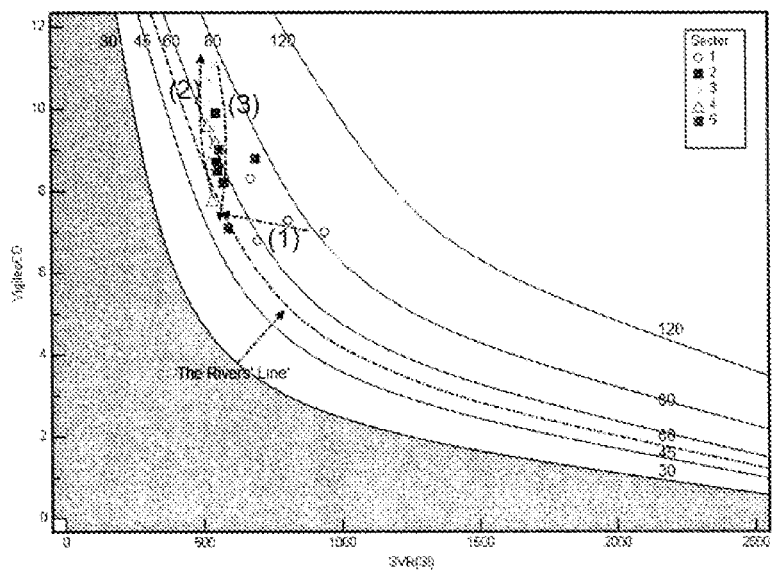
FIG. 29 is an isobar nomogram for the subject in Case Study 5.

The isobar nomogram in FIG. 29 shows a sequential change in pressure, flow and resistance with data points separated at 15 minute intervals. This trending of data is typical of Type 1 shock: a pathological fall in SVR during manipulation of perforation (1) is compensated by an increase in CO (2) followed by a fall in CO with let loss of SPP (3).

Case Study 6 83 yr Female Patient with AS Underwent AVR.

Figure 30:
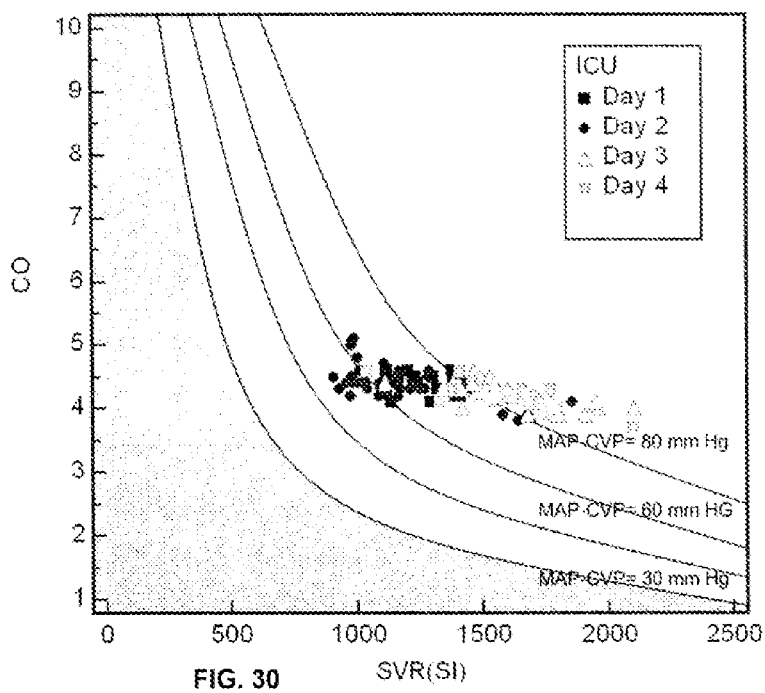
FIG. 30 is an isobar nomogram for the subject in Case Study 6.

Pre-induction haemodynamic values in this patient were CO 3.7, SVR 2480, MAP 125, CVP 11, (MAP–CVP 114). Postoperatively the CO remained essentially constant for 4 days, varying as little as 0.1 to 0.2 L/min in the 72 hours after surgery. 30 hours after surgery, with CO 4.7, SVR 1120, MAP 77, CVP 12 (MAP–CVP 65), the patient exhibited patterns of Type 2 shock and was commenced on metaraminol infusion titrated to SVR>1600. This was only required for 12 hours, and then rapidly weaned. The patient developed no renal dysfunction and had an uneventful postoperative course. FIG. 30 shows CO remained constant post operation and was unchanged with metaraminol infusion (day 3). CO, SVR and SPP were mapped every 30 mins for 72 hours following surgery. If the CO and SVR are mapped against time, it can be seen that CO does not vary, thus SPP is entirely dependent on variation in SVR.

The invention claimed is:

1. A computer-implemented method for generating visual representations of data related to hemodynamic performance in a human or animal subject comprising:
receiving at a data mapping computer processor, first received data measured from the subject over time, from which at least two hemodynamic variables selected from the group including Systemic Perfusion Pressure (SPP), Systemic Vascular Resistance (SVR), Cardiac Output (CO), Heart Rate (HR) and Stroke Volume (SV) are derivable either directly or indirectly or using the equation CO=HR×SV;
operating the data mapping computer processor to transform the first received data corresponding to SVR in such a way that there is an adjustment for pulsatile blood flow caused by left ventricular contractions of the subject, whereby the adjustment produces a new hemodynamic variable referred to as actual Systemic Vascular Resistance (aSVR), where aSVR is calculated as the product of SVR and HR as derived from the first received data;
further operating the data mapping computer processor to process the new hemodynamic variable, aSVR, and the first received data to produce a display signal, the display signal causing a display device to present a visual mapping relating at least two hemodynamic variables according to the new relationship SPP=SV×aSVR; and
displaying the visual mapping on a display device;
wherein the visual mapping presented on the display illustrates trends in the subject's hemodynamic performance over time, as determined from the first received data measured from the subject over time, and transformed by the data mapping computer processor.

2. A method according to claim 1 wherein the visual mapping plots one of:
   (i) SPP in a first dimension and SV in a second dimension;
   (ii) aSVR in a first dimension and SPP in a second dimension; and
   (iii) SV in a first dimension and aSVR in a second dimension.

3. A method according to claim 1 wherein the data mapping computer processor:
   processes the first received data to produce a second display signal; and
   causes the display device to present simultaneously a second visual mapping based on the second display signal according to the relationship CO=HR×SV.

4. A method according to claim 1 wherein the visual mapping includes one or more markers representing a scale for determining a value of a third hemodynamic variable.

5. A method according to claim 1 including the step of color coding in the visual mapping to indicate one or more features in the data selected from the group including: time elapsed; an intervention; gender; and age.

6. A method according claim 1 wherein the data mapping computer processor is programmed to approximate and present on the display, one or more of:
   an autoregulation zone unique to the subject based on the received data or a portion thereof; and
   an autoregulation zone based on a population of subjects having similar physiological profiles.

7. A method according to claim 1 wherein the data mapping computer processor is further programmed to identify in the data one or more patterns associated with a physiological syndrome.

8. A method according to claim 7 wherein the physiological syndrome is shock, and the data mapping computer processor is programmed to classify the shock syndrome into one of type 1, type 2, type 3 or a combination thereof based on the one or more identified patterns.

9. A method according claim 1 wherein the data mapping computer processor is further programmed to quantify a deficit in one or more hemodynamic variables measured from the subject.

10. A method according to claim 1 wherein the data mapping computer processor is programmed to quantify a deficit by:
   (i) determining a difference between the data and a predetermined autoregulation zone unique to the subject; or
   (ii) determining a difference between the data and a predetermined autoregulation zone representative of a population of individuals; or
   (iii) extrapolating data values to a point of intersection representing a notional autoregulation zone unique to the subject.

11. A method according to claim 1 wherein the data mapping computer processor is programmed to perform one or more of:
   (a) identifying automatically non-optimal hemodynamic function in the subject;
   (b) recommending a therapeutic action to restore optimal hemodynamic function in the subject;
   (c) controlling delivery of therapy to a subject, where titration of the therapy under the control of the processor is directed to restoring hemodynamic performance toward an autoregulatory zone applicable to the subject; and
   (d) evaluating the effectiveness of a therapy in an individual subject or a population of individuals.

12. A method according to claim 1 wherein the data is obtained and processed in real-time.

13. A system for generating visual representations of data related to hemodynamic function in a human or animal subject, the system comprising:
- one or more transducers for monitoring continuously over time, at least two hemodynamic variables of the subject selected from the group including Systemic Perfusion Pressure (SPP), Systemic Vascular Resistance (SVR) Cardiac Output (CO), Heart Rate (HR) and Stroke Volume (SV) and generating one or more corresponding first data signals, wherein the hemodynamic variables are obtained from the subject directly or indirectly or using the equation CO=HR×SV;
- a data mapping computer processor receiving the one or more first data signals and configured to transform the first data signals corresponding to SVR to adjust for pulsatile blood flow caused by left ventricular contractions of the subject, whereby the adjustment produces a new hemodynamic variable referred to as actual Systemic Vascular Resistance (aSVR), where aSVR is calculated as the product of SVR and HR as obtained from the subject, the data mapping computer processor being further configured to process the new hemodynamic variable, aSVR and the first data signals to generate a display signal for a visual representation comprising a mapping of at least two hemodynamic variables according to the new relationship SPP=SV×aSVR; and
- a display device receiving the display signal and generating the visual representation;
- wherein the visual mapping presented on the display illustrates trends in the subject's hemodynamic performance over time, as determined from the first received data measured from the subject over time and transformed by the data mapping computer processor, and the subject's hemodynamic function is determinable upon inspection of the trends shown on the display device.

14. A system according to claim 13 wherein the visual representation comprises one or more markers representing a scale for determining a value of a third hemodynamic variable.

15. A system according to claim 13 further including a mode selector for selecting a mode of visual representation of the data; wherein the mode is selected from:
- SPP in a first dimension and SV in a second dimension;
- aSVR in a first dimension and SPP in a second dimension;
- CO in a first dimension and SPP in a second dimension; and
- SV in a first dimension and HR aSVR in a second dimension.

16. A system according to claim 15 wherein the data mapping computer processor produces a second display signal for causing the display to present a second visual mapping of variables according to the relationship CO=HR×SV, and the modes selectable by the mode selector include simultaneous display of the second visual mapping.

17. A system according to claim 13 comprising an analysis module for approximating an autoregulation zone unique to the subject based on the received data or a portion thereof.

18. A system according to claim 13 comprising a diagnosis module for identifying one or more patterns in the data associated with a physiological syndrome.

19. A system according to claim 18 wherein the physiological syndrome is shock and the diagnosis module uses the one or more identified patterns to classify the shock syndrome into one of: type 1, type 2, type 3 or a combination thereof.

20. A system according to claim 13 comprising an analysis module for quantifying a deficit in one or more of the monitored hemodynamic variables from the subject.

21. A system according to claim 20 wherein:
(a) the deficit is quantified by determining a difference between the data and a pre-determined autoregulation zone unique to the subject; or
(b) the deficit is quantified by determining a difference between the data and a pre-determined autoregulation zone representative of a population of individuals; or
(c) the deficit is quantified by extrapolating data values to a point of intersection representing a notional autoregulation zone unique to the subject.

22. A system according to claim 13 comprising a therapy titration module in communication with a therapy set attached to the subject, the therapy titration module controlling titration of therapy from the therapy set.

23. A system according to claim 13 comprising an evaluation module configured to assess hemodynamic data collected during administration of a therapy and to provide an evaluation of the effectiveness of the therapy in maintaining or restoring hemodynamic performance in the subject.

24. A system according to claim 23 wherein the evaluation module evaluates one or both of micro trends and macro trends in the hemodynamic data.

25. A system according to claim 13 comprising an alert module configured to activate an alert automatically when non-optimal hemodynamic performance is detected.

26. A computer program product embodied on a non-transitory memory device containing instructions according to the computer-implemented method of claim 1 and causing the data-mapping computer processor to perform the computer implemented method for determining hemodynamic performance in a human, according to claim 1.

27. A method for generating visual representations of data related to hemodynamic performance in a human or animal subject or in a group of human or animal subjects, the method including the steps of:
- receiving at a data mapping computer data representing two or more hemodynamic variables selected from the group including: (i) Systemic Perfusion Pressure (SPP); (ii) Systemic Vascular Resistance (SVR); (iii) Cardiac Output (CO), (iv) Heart Rate (HR); and (v) Cardiac Output (CO), wherein data representing said variables may be derived from the subject or the group of subjects directly or indirectly or using the equation CO=HR×SV;
- operating the data mapping computer to transform the received data to adjust for pulsatile blood flow caused by left ventricular contractions in the subject or group of subjects, whereby the adjustment produces a new hemodynamic variable referred to as actual Systemic Vascular Resistance (aSVR) where aSVR is calculated as the product of SVR and HR as derived directly or indirectly from the subject or group of subjects;
- operating the data mapping computer to generate on a display operatively coupled to the data mapping computer, a visual representation of data representing hemodynamic variables; and
- approximating from the visual representation the hemodynamic performance of the subject or group of subjects;
- wherein the visual representation includes one or more markers for quantification by the data mapping computer of a third hemodynamic variable, wherein the visual representation comprises a visual mapping of the hemodynamic variables according to the new relationship: SPP=SV×aSVR.

28. A method according to claim 27 wherein the two variables selected for visual representation are:
SPP in a first dimension and SV in a second dimension;
aSVR in a first dimension and SPP in a second dimension; and
SV in a first dimension and aSVR in a second dimension.

29. A method according to claim 27 wherein the visual representation includes simultaneously a mapping of SV and HR.

30. A method according to claim 27 wherein the visual display data causes color coding of the visual mapping to indicate one or more features in the data selected from the group including: time elapsed; an intervention; gender; and age.

31. A method according to claim 27, comprising the step of approximating an autoregulation zone unique to the subject.

32. A method according to claim 27, wherein the hemodynamic data is obtained and used to generate the visual representation in real time.

33. A method according to claim 27, comprising the step of identifying in the data one or more patterns associated with a physiological syndrome.

34. A method according to claim 33, wherein the physiological syndrome is shock and the one or more identified patterns are used to classify the shock syndrome into one of type 1, type 2, type 3 or a combination thereof.

35. A method according to claim 34, wherein:
(a) the deficit is quantified by determining a difference between the data and a pre-determined autoregulation zone unique to the subject; or
(b) the deficit is quantified by determining a difference between the data and a pre-determined autoregulation zone unique to the subject; or
(c) the deficit is quantified by extrapolating data values to a point of intersection representing a notional autoregulation zone unique to the subject.

36. A method according to claim 27, further comprising the step of quantifying a deficit in one or more of the hemodynamic variables in the subject.

37. A method according to claim 27, comprising tailoring therapeutic treatment for the subject so as to restore hemodynamic performance toward the subject's autoregulation zone.

38. A method according to claim 27, comprising the step of automatically identifying non-optimal hemodynamic performance in the subject.

39. A method according to claim 38 comprising the step of automatically activating an alert when the subject's hemodynamic performance is non-optimal.

40. A method according to claim 27 used in a method of evaluating the effect of pharmacological therapy on hemodynamic function.

41. A method according to claim 40 comprising automatically devising a treatment plan or suggesting a therapy for restoring non-optimal hemodynamic performance toward an optimal state.

42. A method according to claim 27 wherein the visual representation provides a continuous mapping of hemodynamic performance in real time.

* * * * *